United States Patent
Mathis et al.

(10) Patent No.: US 8,361,715 B2
(45) Date of Patent: Jan. 29, 2013

(54) METHOD FOR SUPPRESSING A FRET SIGNAL, FRET SIGNAL SUPPRESSOR AGENTS AND USE IN A METHOD FOR MULTIPLEXING BIOLOGICAL EVENTS

(75) Inventors: Gérard Mathis, Bagnols sur Ceze (FR); Eric Trinquet, Pont Saint Esprit (FR); Patrizia Alberti, Paris (FR); Michel Laget, Carsan (FR)

(73) Assignee: CIS Bio International, Saclay (FR)

( * ) Notice: Subject to any disclaimer, the term of this patent is extended or adjusted under 35 U.S.C. 154(b) by 828 days.

(21) Appl. No.: 12/296,790

(22) PCT Filed: Apr. 10, 2007

(86) PCT No.: PCT/EP2007/053479
§ 371 (c)(1),
(2), (4) Date: Oct. 10, 2008

(87) PCT Pub. No.: WO2007/116069
PCT Pub. Date: Oct. 18, 2007

(65) Prior Publication Data
US 2009/0162861 A1  Jun. 25, 2009

(30) Foreign Application Priority Data
Apr. 10, 2006  (FR) ............................ 06 51294

(51) Int. Cl.
*C12Q 1/68*  (2006.01)
*G01N 33/53*  (2006.01)
*G01N 21/76*  (2006.01)
*C12P 19/54*  (2006.01)

(52) U.S. Cl. ............. 435/6.1; 435/7.1; 435/81; 436/172
(58) Field of Classification Search ............... 435/6, 6.1, 435/7.1, 81; 436/172
See application file for complete search history.

(56) References Cited

U.S. PATENT DOCUMENTS

| | | | |
|---|---|---|---|
| 5,455,030 A * | 10/1995 | Ladner et al. | 424/135.1 |
| 6,140,054 A * | 10/2000 | Wittwer et al. | 435/6.12 |
| 6,472,156 B1 | 10/2002 | Wittwer et al. | |
| 6,485,703 B1 * | 11/2002 | Cote et al. | 424/9.1 |
| 6,753,159 B1 | 6/2004 | Lee et al. | |
| 6,878,552 B1 | 4/2005 | Mathis | |
| 2002/0072625 A1 | 6/2002 | Johnson | |
| 2003/0219422 A1 * | 11/2003 | Frauendorf et al. | 424/93.21 |
| 2004/0166553 A1 * | 8/2004 | Nguyen et al. | 435/15 |
| 2005/0118619 A1 | 6/2005 | Xia et al. | |
| 2006/0029938 A1 | 2/2006 | Matsumoto et al. | |

OTHER PUBLICATIONS

Mathis, Clin. Chem., vol. 39, pp. 1953-1959 (1993).*
Watt et al, Immunochemistry, vol. 14, pp. 533-541 (1977).*
Trinquet, E. et al., "D-myo-inositol 1-phosphate as a surrogate of D-myo-inositol 1,4,5-tris phosphate to monitor G protein-coupled receptor activation," Anal. Biochem., Nov. 1, 2006, vol. 358, No. 1, pp. 126-135.

(Continued)

*Primary Examiner* — Robert T. Crow
(74) *Attorney, Agent, or Firm* — Millen, White, Zelano, Branigan, P.C.

(57) ABSTRACT

The invention relates to a method for suppressing the FRET emitted by a reaction medium containing a pair of fluorescent FRET partner conjugates specific for a biological event, characterized in that a FRET signal killer which does not disturb said biological event is introduced into this medium.

16 Claims, 14 Drawing Sheets

Step I:
Detection of X via the $D_1$-A FRET

Step II:
Recognition of $D_1$ by the $F_k$ product and quenching of the $D_1$-A FRET
Detection of Y via the $D_2$-A FRET

OTHER PUBLICATIONS

Bazin, H. et al., "Homogeneous time resolved fluorescence resonance energy transfer using rare earth cryptates as a tool for probing molecular interactions in biology," Spectrochimica Acta, Sep. 14, 2001, vol. 57, pp. 2197-2211.

Bazin, H. et al., "Time Resolved amplification of cryptate emissions: a versatile technology to trace biomolecular interactions," Rev. Mol. Biotech., 2002, vol. 82, pp. 233-250.

Maurel, D. et al., "Cell surface detection of membrane protein interaction with homogeneous time-resolved fluorescence resonance energy transfer technology," Anal. Biochem, Apr. 30, 2004, vol. 329, No. 2, pp. 253-262.

Kennedy, M. E. et al., "Measuring human beta-secretase (BACE1) activity using homogeneous time-resolved fluorescence," Anal. Biochem., Aug. 1, 2003, vol. 319, No. 1, pp. 49-55.

Lopez-Crapez, E. et al., "A separation-free assays for the detection of mutations: combination of homogeneous time-resolved fluorescence and minisequencing," Hum. Mutat., May 2005, vol. 25, pp. 468-475.

Trinquet, E. et al., "Fluorescence technologies for the investigation of chemical libraries," Mol. Biosyst., Aug. 2006, vol. 2, pp. 381-387.

International Search Report for PCT/EP2007/053479 dated Jul. 8, 2007.

* cited by examiner

SEQUENCE LISTING

<160> NUMBER OF SEQ ID NOS: 7

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

```
His His His His His His
1               5
```

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

```
Asp Tyr Lys Asp Asp Asp Asp Lys
1               5
```

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ttgttaacag ctttagtt                                                    18

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aactaacgct ggtaacaagt cgtac                                            25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: Locked nucleic acid
<220> FEATURE:
<221> NAME/KEY: modified_base
<222> LOCATION: (6)..(6)
<223> OTHER INFORMATION: Locked nucleic acid
<220> FEATURE:
<221> NAME/KEY: modified_base
<222> LOCATION: (9)..(9)
<223> OTHER INFORMATION: Locked nucleic acid
<220> FEATURE:
<221> NAME/KEY: modified_base
<222> LOCATION: (15)..(15)
<223> OTHER INFORMATION: Locked nucleic acid
<220> FEATURE:
<221> NAME/KEY: modified_base
<222> LOCATION: (21)..(21)
<223> OTHER INFORMATION: Locked nucleic acid

<400> SEQUENCE: 5
gtacgacttg ttaccagcgt tagtt                                            25

<210> SEQ ID NO 6
<211> LENGTH: 18
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 6
tagaccttga tggttata                                                   18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tataaccatc aaggtcta                                                   18
```

METHOD FOR SUPPRESSING A FRET SIGNAL, FRET SIGNAL SUPPRESSOR AGENTS AND USE IN A METHOD FOR MULTIPLEXING BIOLOGICAL EVENTS

This application is a national stage filing of International Application No. PCT/EP2007/053479, filed Apr. 10, 2007, which claims priority to French Application No. 0651294, filed Apr. 10, 2006.

SEQUENCE LISTING

The instant application contains a Sequence Listing which has been submitted in ASCII format via EFS-Web and is hereby incorporated by reference in its entirety. Said ASCII copy, created on Jun. 20, 2011, is named LOM0055.txt and is 2,425 bytes in size.

Tools that make it possible to measure several events or molecules in a single biological sample are particularly precious. By allowing the multiplexing of biological assays for example, such tools offer new perspectives in the study of complex biological events, but also in the search for new medicaments.

The understanding of certain biological processes and the accurate diagnosis of certain diseases can require the simultaneous detection of several biomolecules and/or biological events. Biological assay multiplexing technology is therefore of notable value in several fields: fundamental research, diagnoses of diseases and also high-throughput screening of molecules potentially active in pharmacology. The term "multiplexing" is intended to mean the possibility of detecting several biomolecules and/or biological events in a single biological sample, contained or occurring in a single reaction volume.

Photoluminescent compounds, i.e. compounds capable of absorbing and re-emitting light, are very suitable for the multiplexing of biological assays.

There are currently two types of multiplexing techniques:
1) Most use several photoluminescent compounds that can be distinguished by their photophysical properties:
    absorption (or excitation) spectrum
    and/or emission spectrum
    and/or luminescence lifetime.
    These techniques require the use of sophisticated instruments capable:
    of exciting the sample at several wavelengths
    and/or of detecting several emission wavelengths
    and/or of distinguishing several luminescence lifetimes.
2) Other techniques, using luminescent compounds, are based on a spatial localization of the biological events to be detected.

Among the existing techniques for multiplexing biological events, mention may be made of:

The technology known under the tradename "DELFIA", sold by the company PerkinElmer, which is a heterogeneous time-resolved fluorometric assay method comprising a signal enhancement step. One particular implementation of DELFIA makes it possible to carry out heterogeneous-phase multidetection assays, based on the use of lanthanide chelates characterized by different lifetimes and different emission spectra. This technique requires the detection of several emission wavelengths and temporal discrimination of the signals (Kimura et al. Forensic Sci Int 2000 September 113:345-51).

The technology known under the tradename "Trupoint", exploited by the company PerkinElmer, which is a method based on the use of, on the one hand, lanthanide chelates and, on the other hand, fluorescence quenchers, and on time-resolved measurement of fluorescence. One particular implementation of this technique, consisting in using several rare earths emitting at various wavelengths, makes it possible to carry out multidetection assays. This technique requires the measurement of fluorescence at several emission wavelengths and temporal discrimination of the signals.

A certain number of techniques based on nucleic acid polymerase chain reactions (known as "PCR") allow the quantitative detection of nucleic acids.

Techniques known under the tradenames "TaqMan", "Molecular Beacon", "Scorpion", "Invader", "LightCycler" and "Amplifluor" use fluorophores and can be adapted to multidetection, using several fluorophores characterized by different emission spectra. These techniques require the detection of the fluorescence emitted by each of these fluorophores, at various emission wavelengths.

Some authors have described a homogeneous-phase multidetection technique based on the detection of the polarization of fluorescence of several tracers at various emission wavelengths (Lynch et al., 1999; Blommel et al., 2004).

In the microscopy field, it is common practice to use several fluorescent compounds simultaneously in cell labeling. These techniques require the combined use of several excitation and emission wavelengths. Confocal microscopy systems require, in addition, several excitation sources.

The technology exploited under the tradename "FMAT" (Fluorometric Microvolume Assay technology), developed by the companies Beckton Dickinson and PerkinElmer Biosystems, is based on the use of a LASER which scans microwell plates. This technique makes it possible to measure biological events by multiplexing, but requires the combined use of several excitation and emission wavelengths in addition to the spatial localization of the signal via the LASER (Swartzman et al., 1999).

The technology known under the tradename "xMAP" from the company Luminex is based on the use of colored microspheres separated by flow cytometry. The multiplexing of the technology is based on the use of several excitation and detection sources. The assay does not really take place in a homogeneous phase: the content of each well is drawn up so as to pass into the flow cytometry system.

The company Meso Scale Discovery has developed a homogeneous-phase technology which allows the multiplexing of biological assays using a single luminescent compound. This technology is based on the spatial localization of each analyte to be detected: the reaction volume is deposited into a well of a microplate, and the various analytes are captured and detected on distinct points pre-deposited on the bottom of the well.

The technologies developed by the companies Luminex and Meso Scale Discovery allow a high degree of multiplexing; on the other hand, they are not suitable for the detection of biomolecules inside intact cells or in a homogeneous medium, since a solid support is required.

The technology known under the tradename "eTag™" from the company Aclara is technology which allows the multiplexing of biological assays using a single excitation wavelength and a single emission wavelength. Nevertheless, it requires the discrimination of each probe by capillary electrophoresis. It is in fact based on the use of probes characterized by the same fluorescence properties, but having various mass/charge ratios (Chan-Hui et al. 2004; Tian et al. 2004).

Bradford et al. (2004) have described a multidetection system combining flow cytometry and fluorescence intensity: the use of the indirect labeling system developed by Molecular Probes (ZENON technology) makes it possible to obtain fluorescent conjugates, each having a defined fluorescence intensity. Each antibody-fluorescent compound conjugate is directed against a given cell surface antigen. By detecting the fluorescence in a flow cytometer, it is possible to determine the percentage of cells expressing one surface antigen or another as a function of the fluorescence intensity measured on the cells.

Some additional articles present fluorescent compounds that may allow the implementation of multiplexed assays:

Kurner et al., 2001, describe phosphorescent nanospheres (sold by the company Chromeon) characterized by different lifetimes and different emission wavelengths, which can be excited at the same wavelength.

Tong et al. (2001) describe the use of 3 fluorophores for the production of 8 probes, which can be excited at the same wavelength; 3 detection wavelengths are necessary for identifying the probes (technique known as "CFET tags", for "Combinatorial fluorescence energy transfer tags").

Tyagi et al. (2000) describe molecular beacons consisting of nucleic acids labeled with fluorophores, which can be excited at the same wavelength and which emit at different wavelengths.

The prior art techniques are therefore all based on measuring equipment for discriminating between the signals emitted by the reaction medium: equipment for measuring light signals emitted at various wavelengths, equipment for separating the signals by electrophoresis (etags), devices for specific spatial localization of each biological event studied, and therefore of each signal.

The use of these techniques for the multiplexing of biological events is not therefore always easy since most of the time they require complex equipment, or else separating or washing steps, which are not always suited to the needs of the pharmaceutical industry, in particular the needs in the high throughput screening field.

A certain number of compounds having a fluorophore-binding domain have been described, as have their possible effects on the photophysical properties of the fluorophores that they recognize.

U.S. Pat. No. 6,747,135 discloses polypeptides, termed "fluorettes", which have a high affinity for fluorophores. These fluorettes are particularly useful for coupling fluorophores to proteins noncovalently. Moreover, this patent discloses a fluorette specific for Texas red, which causes a shift in the absorption and emission spectra of this fluorophore. The other fluorettes presented have no significant effect on the fluorescence properties.

Watt et Al (1977) describe the fact that the binding of an anti-fluorescein antibody to fluorescein modifies the photophysical properties of the latter: 90% decrease in its quantum yield, shift in its maximum emission and excitation wavelengths.

Patent application US 2005/0064512 discloses polypeptides, in particular antibodies, which specifically bind organic fluorophores, especially of the cyanin family. The antibodies according to US 2005/0064512 bring about changes in the photophysical properties of these fluorophores and in particular a considerable change in their excitation and emission maxima.

Babendure et al., 2003, describe short nucleotide sequences (termed aptamers) capable of binding to organic fluorophores such as those comprising a triphenylmethane unit. The authors have, moreover, demonstrated an increase in the fluorescence emitted when the aptamer binds to the fluorophore.

The company Molecular Probes sells a certain number of antibodies, most of which are polyclonal antibodies, having an affinity for fluorophores such as anti-fluorescein antibodies, anti-Alexa Fluor 488 antibodies, anti-tetramethylrhodamine antibodies, anti-Bodipy antibodies or anti-dansyl antibodies. These antibodies modify the properties of the fluorophores to which they bind: they cause quenching or, on the contrary, enhancement of fluorescence.

These compounds all have a fluorophore-binding domain and some of them cause variations in the spectroscopic properties when they bind to the fluorophore, but none of them has been described as a FRET killer. Furthermore, it will be noted that their effects are not homogeneous, since some will shift the emission or excitation spectra, others will cause fluorescence enhancement or quenching, and, finally, others will not modify the characteristics of the fluorophores.

DESCRIPTION OF THE INVENTION

The applicant has discovered a method for suppressing a FRET ("Fluorescence Resonance Energy Transfer") signal. This method has allowed the development of methods for multiplexing biological events in a reaction medium. Certain means used in these methods are also the subject of the present invention, in particular certain FRET signal killers, and also kits of parts for implementing the methods according to the invention.

The multiplexing methods according to the invention have many advantages compared with the prior art methods, since they can be carried out in a homogeneous medium, do not require any separating or washing step, and can be used with the fluorimeters normally used for detecting a single biological event. Furthermore, these methods do not require time resolution of the signals or spatial localization of the biomolecules to be detected.

The methods according to the invention are based on the FRET technique, which consists in measuring the nonradiative resonance energy transfer between a donor fluorophore and an acceptor fluorophore. After light excitation at the excitation wavelength of the donor fluorophore, energy transfer takes place between the donor fluorophore and the acceptor fluorophore if they are close to one another.

The FRET phenomenon can be detected by measuring various parameters of the fluorescence signal emitted either by the donor or by the acceptor, or by the two molecules. Among the techniques most commonly used, mention may in particular be made of:

measuring the decrease in donor fluorescence induced by the FRET phenomenon;

measuring the increase in acceptor fluorescence induced by the energy originating from the donor through the FRET;

determining the [(acceptor fluorescence increase)/(donor fluorescence decrease)] ratio;

measuring the decrease in the donor fluorescence lifetime induced by the FRET phenomenon. This is in particular measured by the "Fluorescence Lifetime Imaging Microscopy" (FLIM) technique;

measuring the increase in the fluorescence of the donor involved in a FRET after photobleaching of the acceptor. This photobleaching technique is known as Fluorescence Recovery After Photobleaching (FRAP).

The FRET technique is a technique of choice for studying chemical or biological interactions which cause a modification of the distance between a donor fluorophore and an acceptor fluorophore: the general principle consists in preparing fluorescent conjugates by coupling the FRET partners to molecules involved in a biological process or to probes which recognize such molecules, and in measuring the variations in FRET in response to a stimulation, for example by adding, to the medium, compounds which will affect the biological process studied. These compounds may, for example, be involved in the regulation of enzyme reactions, causing modifications to the three-dimensional conformation of proteins, causing the production of an analyte and the formation of an analyte/FRET partners complex; in all cases, a modification of the biological event studied causes a modification of the FRET between the fluorescent donor and acceptor compounds.

I—Method for Suppressing FRET

The applicant has now developed a method based on suppressing the FRET between two fluorescent FRET partner conjugates specific for a biological event, not by intervening on this biological event, but by intervening on the FRET partners.

One of the subjects of the invention is therefore a method for suppressing the FRET emitted by a reaction medium containing a pair of fluorescent FRET partner conjugates specific for a biological event, characterized in that at least one FRET signal killer is introduced into this medium, said FRET signal killer not disturbing said biological event.

This method may be used in the context of the study of many biological events, such as: the biological events involving enzyme reactions (such as activities of kinase, phosphorylase, transferase, hydrolase, lyase, ligase, isomerase, polymerase, etc., type), the presence or the variation in concentration of an analyte in the reaction medium (for example, the presence or variation in concentration of proteins, enzymes, enzyme substrates, intracellular messengers, such as cyclic nucleotides (cAMP, cGMP, etc.), phospholipids (PIP2, PIP3, etc.), transcription factors, compounds comprising an inositol ring (IP1, IP2, IP3, IP4. etc.), nucleic acids, growth factors, the coming together of two molecules in the reaction medium, or modifications to the three-dimensional conformation of molecules. The examples described illustrate some uses of the invention, but it would be unjustified to limit the invention to these events.

The applicant has demonstrated, surprisingly, that certain compounds can suppress the FRET signal resulting from 2 FRET partner conjugates coming closer together.

The term "FRET signal killer" is intended to mean a compound which causes a decrease in FRET signal of at least 70% compared with the signal measured in the absence of this compound. The FRET signal killers which cause a decrease in FRET of at least 80%, or of at least 90%, are preferred.

The FRET signal killers used in the method according to the invention do not disturb the biological event studied insofar as they act on one of the fluorophores involved in the FRET, and not on the biological event studied: they have no effect on the distance separating the molecules involved in the biological event.

In order to determine whether a compound is a FRET signal killer within the meaning of the invention, it can be brought into contact with a pair of fluorescent FRET partner conjugates emitting a FRET signal, for example two fluorescent conjugates which recognize the same molecule, or else two fluorescent conjugates of which one comprises a biotin and the other streptavidin; the FRET signal emitted by the reaction medium is measured in the presence and absence of said compound, the FRET signal killers being those which cause a decrease in signal of at least 70%. This simple test allows those skilled in the art to isolate FRET killers within the meaning of the invention.

These agents may be of different nature, and have various functions, but in all cases make it possible to suppress the FRET signal emitted by a given donor-acceptor pair:

a) FRET Signal Killers Acting by Specific Attachment by Noncovalent Binding to One of the Fluorophores Involved in the FRET.

These agents have a domain which allows specific and noncovalent binding with the fluorophore, and can be chosen from: proteins, in particular antibodies or antibody fragments, peptides or aptamers, each having a binding domain for one of the FRET partner fluorophores.

Those skilled in the art have techniques available to them which make it possible to produce these compounds, and to test their binding with fluorophores (for example, conventional antibody production techniques, or else the "SELEX" method for selecting aptamers).

In the case of a FRET involving a rare earth cryptate or chelate, preferred FRET signal killers are compounds capable of binding noncovalently to rare earth cryptates or chelates, for instance: proteins, in particular antibodies or antibody fragments, peptides, or aptamers which have a binding domain for a rare earth cryptate or chelate.

FRET signal killers that are even more preferred are anti-rare earth chelate or anti-rare earth cryptate antibodies.

The anti-cryptate antibodies are produced by techniques, well known to those skilled in the art, for immunizing a mammal with an antigen.

When the antigen is small, as is the case of the rare earth cryptate, it should be coupled to an immunogenic carrier molecule. For this, the cryptate is functionalized, as described in patent EP 321 353. Preferably, an alkylamine arm is grafted to the cryptate.

The carrier molecules may be chosen from: bovine serum albumin (BSA) or cationic BSA (cBSA), KLH (Keyhole Limpet Hemocyanin), thyroglobulin, and ovalbumin. The carrier molecules may also be liposomes or synthetic carrier molecules, such as L-lysine polymers or L-glutamic acid polymers, ficoll, dextran, or else polyethylene glycol. These carrier molecules generally comprise functional groups which will react with the functionalized cryptate, or alternatively such groups may be introduced by conventional techniques. Preferably, a rare earth cryptate bearing an alkylamine group is conjugated to BSA.

The immunogen thus obtained is subsequently mixed with an adjuvant, for instance Freund's adjuvant.

Mammals—for example mice—are immunized by subcutaneous injection of this solution, and after a period required for the induction of immunity, the sera of the animals are collected and the polyclonal antibodies are purified, for example by affinity chromatography.

The anti-cryptate monoclonal antibodies are produced by using various techniques known to those skilled in the art. By way of example, mention may be made of the technique derived from the studies by Köhler and Milstein: a few weeks after the immunization, the spleen of the mouse immunized with the antigen is removed. A mixture of lymphocytes and plasma cells originating from this spleen is fused, in vitro, with myeloma cells in the presence of a cell-fusion inducer, such as polyethylene glycol. A mutant myeloma cell line, devoid of hypoxanthine guanosine phosphoribosyl transferase (HGPRT), is used so as to make it possible to readily select the hybrid cells. These cells are cultured in a medium containing hypoxanthine, aminopterin (methotrexate) and thymine (HAT medium) in order to eliminate the nonfused myeloma cells and to select the hybrids of interest. The nonfused spleen cells die because they are incapable of proliferating in vitro. The hybrid cells, on the other hand, survive. The hybridomas thus obtained are cultured in the wells of a cell culture plate. The supernatants of these wells are tested for the presence of specific anti-rare earth cryptate antibodies in a simple screening assay such as ELISA or RIA. The hybridomas are subsequently cloned and can be injected into mammals so as to induce myelomas secreting a large amount of anti-cryptate antibodies into the ascites fluid.

Anti-rare earth cryptate polyclonal or monoclonal antibodies obtained can subsequently be tested for their ability to suppress the FRET signal emitted by a pair of FRET partners comprising said rare earth cryptate as energy donor. For this, the process can be carried out as described below and in example 1 presented hereinafter.

b) FRET Killers Acting by Uncoupling of the Fluorophore with the Biological Event.

As described above, the study of biological events using the FRET phenomenon is based on the labeling of molecules involved in the biological event with FRET partner fluorophores. If this labeling is carried out noncovalently, via binding partners, it is possible to uncouple one of the fluorophores from the biological event.

For example, if a molecule involved in the biological event is covalently bound to a member of a pair of binding partners (for example, a single-stranded oligonucleotide), and the fluorophore is covalently bound to the other member of this pair (for example, a complementary single-stranded oligonucleotide), then the addition, to the measuring medium, of a first member of this pair (the first single-stranded oligonucleotide, in free form) will uncouple the labeling of the biological molecule by the fluorophore, by means of a phenomenon of competition according to the scheme represented in FIG. 1.

These FRET signal killers are therefore members of binding-partner pairs, and of course can only be used as FRET signal killers if their partner is grafted to the molecule involved in the biological event studied. They can be chosen from the members of the following pairs: complementary single-stranded nucleic acids, tag/anti-tag, and in particular the members of the pairs: DNP/anti-DNP antibody, in which DNP represents dinitrophenol; GST/anti-GST antibody, in which GST represents glutathione S-transferase; biotin/avidin; 6HIS/anti-6HIS antibody ('6HIS' disclosed as SEQ ID NO: 1), in which 6HIS is a peptide consisting of 6 histidines (SEQ ID NO: 1); Myc/anti-Myc antibody, in which Myc is a peptide consisting of amino acids 410-419 of the human Myc protein; FLAG®/anti-FLAG® antibody, in which FLAG® is a peptide having the following 8 amino acids DYKDDDDK (SEQ ID NO: 2); HA/anti-HA antibody, in which HA is an epitope of influenza hemagglutinin.

c) FRET Killers Acting by Modifying the Nature of the Fluorophore

In the case where the fluorophore is a rare earth chelate, the FRET killers may reduce the stability of the fluorophore, by competing either with the rare earth for the binding with the chelate, or with the chelate for the binding of the rare earth.

For example, the addition to the measuring medium of an ion which will compete with the rare earth for the binding with the chelate may promote the formation of a new non-fluorescent chelate-ion complex. Such an ion may be the manganese ion $Mn^{2+}$ in the case of rare earth chelates.

By way of example of competition with the chelate, mention may be made of the use of metal-complexing agents, such as EDTA, which will result in the formation of a non-fluorescent EDTA-rare earth complex, to the detriment of the fluorescent chelate-rare earth complex.

Moreover some fluorophores are sensitive to variations in ionic strength of the medium: this is in particular the case of protein fluorophores comprising several subunits linked by electrostatic bonds, and the quaternary structure of which will be destabilized when there is a decrease in the ionic strength of the medium. By way of example, mention may be made of the case of allophycocyanin, which dissociates under these conditions. When such fluorophores are used, the FRET signal may therefore be suppressed by decreasing the ionic strength of the reaction medium.

d) FRET Killers Acting by Modifying the Photophysical Properties of the Fluorophore FRET killers of this type bring about a fluorescence quenching effect.

By way of example, mention may be made of uric acid which, in the case where the fluorophore is a rare earth chelate or cryptate, can cause rare earth oxidation-reduction reactions which can result in suppression of the FRET.

Other fluorophores are sensitive to variations in pH and, in this case, pH modifiers can also be used as FRET signal killers.

In general, agents which modify the emission or absorption spectrum of a fluorophore, or else those which inhibit the fluorescence, may be used in the methods according to the invention, provided that they effectively cause suppression of the FRET signal for the purpose of the invention. This characteristic can be tested simply, as mentioned above.

Pair of Fluorescent FRET Partner Conjugates.

For the purpose of the invention, a pair of fluorescent FRET partner conjugates consists of a fluorescent donor conjugate and a fluorescent acceptor conjugate, the emission and absorption spectra of which are compatible. Each of these conjugates consists of a fluorophore covalently bound to a probe, this probe being involved in a biological event, or else specifically recognizing a molecule involved in a biological event.

The notion of FRET partners is well known to those skilled in the art, who are capable, on the basis of the spectroscopic characteristics of the known fluorescent compounds, of selecting pairs of fluorophores that are compatible in terms of FRET. Reference may, in addition, be made to the book by Lakowicz, Principles of fluorescence spectroscopy, $2^{nd}$ edition, Kluwer academic/plenum publishers, NY (1999). Moreover, the term "FRET" is used here in the broad sense and includes time-resolved FRET (TR-FRET).

Fluorophores:

The fluorophores may be chosen from the following group comprising: luminescent proteins, such as green fluorescent protein (GFP) or variants thereof, fluorescent proteins extracted from coral, phycobiliproteins, such as B-phycoerythrin, R-phycoerythrin, C-phycocyanin, allophycocyanins, in particular those known under the name XL665; luminescent organic molecules, such as rhodamines, cyanins, squaraines, fluorophores known under the name BODIPY, fluoresceins, compounds known under the name AlexaFluor; supramolecular complexes, such as rare earth cryptates, rare earth chelates (in particular europium, terbium, samarium, dysprosium and neodymium chelates and cryptates); luminescent inorganic particles such as quantum dots; these fluorophores may be used either as donors or as acceptors in a FRET system.

The rare earth complexes are known compounds which are described, for example, in U.S. Pat. No. 4,761,481, U.S. Pat. No. 5,032,677, U.S. Pat. No. 5,055,578, U.S. Pat. No. 5,106,957, U.S. Pat. No. 5,116,989, U.S. Pat. No. 4,761,481, U.S. Pat. No. 4,801,722, U.S. Pat. No. 4,794,191, U.S. Pat. No. 4,637,988, U.S. Pat. No. 4,670,572, U.S. Pat. No. 4,837,169 and U.S. Pat. No. 4,859,777. Other chelates are composed of a nonadentate ligand such as terpyridine (EP 403 593, U.S. Pat. No. 5,324,825, U.S. Pat. No. 5,202,423, U.S. Pat. No. 5,316,909). The rare earth may be europium or terbium.

The rare earth cryptates are described in patents EP 0 180 492 and EP 0 601 113 and application WO 01/96 877.

Advantageously, the rare earth complex is a europium chelate or cryptate. When the rare earth is europium, the rare earth complex is preferably a rare earth cryptate comprising a pyridine unit, even more preferably comprising a pyridine-bipyridine unit.

Probes:

The probe present in a fluorescent conjugate may be a molecule directly involved in the biological event studied, or alternatively a molecule which recognizes another molecule involved in said event, for example an anti-protein of interest antibody, in the case where the biological event is an interaction between two proteins of interest.

In general and according to the invention, the notion of molecule involved in a biological event means that this molecule plays a role in the biological event, or else is recruited to or has a tendency to accumulate on the site of the biological event. For example, if the biological event is the production of an analyte, a molecule involved in this event may be: a precursor of the analyte, an enzyme that participates in the synthesis of this analyte, or an antibody which recognizes the analyte.

The molecules involved in biological events may be: proteins, peptides, enzymes, enzyme substrates, intracellular messengers such as cyclic nucleotides (cAMP, cGMP, etc.), phospholipids (PIP2, PIP3, etc.), transcription factors, compounds comprising an inositol ring (IP1, IP2, IP3, IP4, etc.), nucleic acids, oligonucleotides or growth factors.

The compounds which recognize molecules involved in biological events may be: antibodies or antibody fragments, anti-tag antibodies or antibody fragments which recognize tags grafted onto the molecules involved in the biological events, aptamers, peptides, proteins, single-stranded nucleic acids that can hybridize with a complementary sequence grafted onto the molecules involved in biological events. The tag/anti-tag systems commonly used include the pairs: DNP/anti-DNP antibody, in which DNP represents dinitrophenol; GST/anti-GST antibody, in which GST represents glutathione S-transferase; biotin/avidin; 6HIS/anti-6HIS antibody ('6HIS' disclosed as SEQ ID NO: 1), in which 6HIS is a peptide consisting of 6 histidines (SEQ ID NO: 11; Myc/anti-Myc antibody, in which Myc is a peptide consisting of amino acids 410-419 of the human Myc protein; FLAG®/anti-FLAG® antibody, in which FLAG® is a peptide having the following 8 amino acids DYKDDDDK (SEQ ID NO: 2); HA/anti-HA antibody, in which HA is an epitope of influenza hemagglutinin.

The probes will therefore determine the specificity of a pair of fluorescent FRET partner conjugates for a given biological event. The method according to the invention may be used for studying many biological events, such as: biological events involving enzyme reactions (such as activities of kinase, phosphorylase, transferase, hydrolase, lyase, ligase, isomerase, polymerase, etc., type), the presence or the variation in concentration of an analyte in the reaction medium (for example, the presence or variation in concentration of proteins, enzymes, enzyme substrates, intracellular messengers such as cyclic nucleotides (cAMP, cGMP, etc.), phospholipids (PIP2, PIP3, etc.), transcription factors, compounds comprising an inositol ring (IP1, IP2, IP3, IP4, etc.), nucleic acids, growth factors), two-molecules coming closer together in the reaction medium, or modifications to the three-dimensional conformations of molecules. The examples described hereinafter illustrate some uses of the invention, but it would be unjustified to limit the invention to these events.

Those skilled in the art are able to prepare pairs of fluorescent FRET partner conjugates specific for a biological event: the conjugation of a fluorophore with a probe for the purpose of the invention is in fact widely described in the literature (for example, in "Bioconjugate Techniques", G. T. Hermanson, Academic Press, 1996) and employs the use of the reaction groups conventionally used.

The method for suppressing the FRET signal in a reaction medium is particularly useful when several FRET signals derived from several pairs of fluorescent FRET partner conjugates, specific for several biological events, must be measured: it in fact makes it possible to detect biological events by multiplexing.

II—Method for Multiplexing Biological Events

Another subject of the invention is a method for detecting at least two biological events in the reaction medium, which consists:

1) in introducing into this medium:
   at least 2 pairs of fluorescent FRET partner conjugates, each pair being specific for one of the biological events studied, the wavelength at which the fluorescent donor conjugates are excited being the same for all the pairs, and the wavelength at which the signals emitted by the fluorescent acceptor conjugates are measured being the same for all the pairs;
   killers of the FRET signal between two given FRET partners, with there being no disturbance of the biological events studied, these compounds being introduced into the medium sequentially; and
2) in sequentially measuring the various FRET signals emitted by the reaction medium.

According to the invention, the method for detecting n biological events in a reaction medium comprises the following steps:
(i) bringing the reaction medium into contact with a first pair of fluorescent FRET partner conjugates specific for a first biological event;
(ii) exciting the reaction medium at the wavelength $\lambda 1$;
(iii) measuring the FRET signal emitted by the reaction medium at the wavelength $\lambda 2$ (signal corresponding to the first biological event);
(iv) adding a FRET signal killer specific for the last pair of FRET partners brought into contact in the medium;
(v) bringing the reaction medium into contact with a pair of fluorescent FRET partner conjugates specific for a biological event different than that (those) detected in the preceding steps;
(vi) exciting the reaction medium at the wavelength $\lambda 1$;
(vii) measuring the FRET signal emitted by the reaction medium at the wavelength $\lambda 2$ (signal corresponding to the biological event for which the last pair of FRET partners brought into contact in the medium is specific);
steps (iv) to (vii) being repeated (n−2) times, n being an integer between 2 and 10, i.e. equal to 3, 4, 5, 6, 7, 8, 9, or 10.

The fluorescent FRET partner conjugates comprise a donor fluorophore and an acceptor fluorophore, $\lambda 1$ being the excitation wavelength of the donor fluorophores and $\lambda 2$ being the emission wavelength of the acceptor fluorophores.

The fluorescent FRET partner conjugates and the FRET signal killers have been defined above.

The expression "bringing the reaction medium into contact with a pair of fluorescent FRET partner conjugates specific for a biological event" means that the FRET partners are in the reaction medium simultaneously. This result can be achieved by introducing them simultaneously during either of steps (i) and (v), or alternatively by introducing them sequentially into the reaction medium: in this case, the bringing into contact will correspond to the addition of the second member of this pair, on the condition that its partner has already been introduced in a prior step, for example during step (i). According to the invention, the pair of fluorescent FRET partner conjugates are in fact formed sequentially.

Thus, in a particular embodiment of the method according to the invention, step (i) consists in introducing, on the one hand, a member of each of the n pairs of fluorescent FRET partner conjugates specific for the n biological events to be studied (i.e. n members of n pairs) and in introducing, on the other hand, a second member of one of these pairs so as to effectively bring into contact the pair of fluorescent FRET partner conjugates specific for the first biological event to be detected. The second members of the other pairs of fluorescent FRET partner conjugates are introduced successively, in each of the subsequent steps (v).

In another embodiment, the members of the pairs of fluorescent FRET partner conjugates are introduced simultaneously into the measuring medium, the first pair being introduced into the reaction medium in step (i), and the other pairs being introduced successively in each of the steps (v).

The above method is based on the principle of the sequential formation of pairs of FRET partners and the sequential measurement then quenching of the associated FRET signal. Each signal measured is representative of a given biological event.

An alternative method consists in introducing all the n pairs of FRET partners into the measuring medium, in measuring the total signal emitted and corresponding to the sum of the signals specific to each biological event, and then in sequentially introducing the FRET killers and in measuring the signal emitted after each step of introducing said killers. The set of measurements makes it possible, by means of a simple mathematical method, to calculate the value of the signal specific to each pair of FRET partners and therefore to each biological event.

In practice and by way of example for 3 biological events, the following measurements are carried out:
A=S1+S2+S3 (sum of the signals corresponding to each biological event);
B=S1+S2 (measurement after addition of a FRET killer for the FRET between the fluorophores specific for event 3);
C=S1 (measurement of addition of FRET killers for the FRET between the fluorophores specific for events 3 and 2).
Since the values A, B and C are known (measured), those of the signals S1, S2 and S3 can be readily calculated.

This alternative method for detecting n biological events in a reaction medium comprises the following steps:
(i) bringing the reaction medium into contact with the n pairs of fluorescent FRET partner conjugates specific for n biological events;
(ii) exciting the reaction medium at the wavelength $\lambda 1$;
(iii) measuring the FRET signal emitted by the reaction medium corresponding to all the biological events studied;
(iv) introducing into the reaction medium a FRET signal killer specific for one of said pairs of fluorescent FRET partner conjugates, where appropriate different than those introduced in the preceding steps;
(v) exciting the reaction medium at the wavelength $\lambda 1$;
(vi) measuring the FRET signal emitted by the reaction medium, corresponding to all the reaction events minus those of which the signal was blocked in a preceding step; steps (iv) to (vi) being repeated (n−1) times, n being an integer between 2 and 10, i.e. equal to 3, 4, 5, 6, 7, 8, 9 or 10;
(vii) determining the FRET signal values for each of the n biological events, by mathematical resolution of the n equations obtained in the steps (iii) and each of the steps (vi).

The fluorescent FRET partner conjugates comprise a donor fluorophore and an acceptor fluorophore, $\lambda 1$ being the excitation wavelength of the donor fluorophores and $\lambda 2$ being the emission wavelength of the acceptor fluorophores.

As described above, the methods according to the invention involve several pairs of fluorescent FRET partner conjugates specific for a given biological event. Each pair consists of two conjugates, each comprising a fluorophore covalently coupled to a specific probe. It is entirely possible for some pairs to have common elements: Two given pairs may thus share the same donor conjugate, the same acceptor conjugate, or else comprise the same donor fluorophores or the same acceptor fluorophores.

Some pairs share a fluorescent conjugate, in other words, one of the fluorescent conjugates will have several FRET partners. For example, a first pair may consist of a fluorophore1-probe1 member and a fluorophore2-probe2 member, and the other pair may consist of a fluorophore1-probe1 and fluorophore3-probe3 member.

Some pairs may comprise the same fluorophores, but in this case, they differ in terms of their probes: for example a first pair may consist of a fluorophore1-probe1 member and a fluorophore2-probe2 member, and the other pair may consist of a fluorophore1-probe3 and fluorophore3-probe4 member.

In the methods according to the invention, each FRET signal killer used is specific for a single pair of FRET partners. This is one of the essential characteristics of the invention which makes it possible to differentiate between the signals corresponding to each biological event that it is desired to study.

Time-resolved FRET techniques offer certain advantages for studying biological events which take place in biological media. Thus, in one particular embodiment of the methods according to the invention, the fluorescent FRET partner conjugates are TR-FRET (time-resolved FRET) partners.

The study of biological events may require a step of stimulating the reaction medium in order to trigger or cause to vary the biological events that it is desired to study. This stimulation may in particular be of chemical, pharmacological, electrical, thermal or mechanical nature.

For example, if the biological event studied is the production of an analyte in a cell in response to the stimulation of a transmembrane receptor, it will be necessary to add an agonist of said receptor.

In one particular embodiment, the stimulation step consists in adding to the reaction medium an agonist, an antagonist, an allosteric modulator or an inverse agonist of a given receptor.

Insofar as the methods according to the invention make it possible to study several biological events in the same reaction medium, it may be necessary to carry out several stimulations.

Moreover, the same stimulation may activate several parallel signaling pathways or alternatively a cascade of signaling pathways and therefore several biological events that can be detected by virtue of the methods according to the invention. In this case, these methods will comprise only one stimulation step, which will cause a variation in the various biological events to be detected. Mention may be made of the example of a pharmacological stimulation which brings about the activation of protein kinases (biological event 1) which will themselves bring about the phosphorylation of proteins (event 2).

The methods according to the invention make it possible to detect several biological events and therefore, of course, the variation in said events in the presence of agents of which it is desired to determine the effect on several biological events taking place in the reaction medium. The methods according to the invention may therefore be advantageously used in a method for screening for biologically active compounds which may be of use, for example, as medicaments. For this, the method according to the invention may comprise a step of adding a test compound to the reaction medium.

The method according to the invention may be carried out in various reaction media, in particular media comprising a mixture of biological compounds, such as a mixture of proteins, of antibodies, of nucleic acids, of intracellular messengers, of extracellular messengers, etc. The reaction medium may also contain cells originating from cell cultures, cells obtained by tissue dissociation, permeabilized cells, ground cellular material, or membrane preparations.

The reaction medium is, moreover, contained in a container conventionally used, for example a microplate well, or a cell incubation chamber suitable for a microscope.

Those skilled in the art are able to understand that the method according to the invention cannot be limited to specific reaction media so long as these reaction media comprise the materials essential for studying the biological events targeted: by way example, if the biological events are enzyme reactions, the reaction medium will have to comprise the corresponding enzymes and substrates.

The multiplexing methods according to the invention which make it possible to simultaneously detect several biological events are particularly advantageous in the following applications:

Detection of Molecules Secreted Simultaneously by Cells.

For example, detection of the various cytokines secreted in response to a stimulation of the cell makes it possible to refine understanding of the mechanisms of intercellular communication: in this case, the pairs of fluorescent FRET partner conjugates will each be specific for a given cytokine.

Another example consists in detecting and quantifying beta-amyloid peptides: in patients suffering from Alzheimer's disease, an increase in the Aβ-42 amyloid peptide/Aβ-40 peptide ratio has been observed. The methods of the invention, which make it possible to measure the various amyloid peptides secreted by the same cell or cell culture, greatly facilitate the understanding of the mechanisms of development of amyloid plaques and the search for medicaments capable of acting on the concentration of each of the amyloid peptides. In view of this application, the methods according to the invention will comprise the use of FRET partner conjugates for detecting these peptides.

Parallel Examination of Various Cell Signaling Pathways (Examples: Simultaneous Assay of Second Messengers or Other Mediators).

It is particularly advantageous, in the study of cell processes, to be able to obtain information on the various signaling pathways simultaneously activated in a cell in response to an extracellular stimulation.

The methods according to the invention are particularly advantageous for simultaneously detecting the signaling pathways involving Gs, Gi, Gq or G11/G12 proteins, and the small G proteins, Ras, Rho, Rab or Ran proteins.

The intracellular signaling pathways can be measured in particular by detecting the following events:
stimulation or inhibition of adenyl cyclase, for example by measuring the amount of cAMP in the cell;
activation of phospholipase C, for example by measuring the amount, in the cell, of compounds containing inositols (IP3, IP1, IP2, etc.), DAG;
activation of GPCR kinases (GRKs);
translocation of beta-arrestin.

Those skilled in the art are familiar with these various signaling pathways, which are cited only by way of limitation. Fluorescent FRET partner conjugates specific for each of these signaling pathways can be used in the methods according to the invention: they may consist of a fluorophore and antibodies specific for a molecular characteristic of a given signaling pathway (IP3, cAMP etc.), labeled with FRET partners, or else a molecule involved in one of these signaling pathways, labeled with a fluorescent compound: beta-arrestin coupled to a fluorophore, G-protein membrane receptor subunit coupled to a fluorophore.

It has recently been shown that certain membrane receptors, in particular GPCRs, bring about the activation of various intracellular signaling pathways as a function of the agonist which binds to their extracellular domain. This phenomenon is known as "agonist trafficking".

The methods according to the invention are ideal for studying these "agonist trafficking" phenomena since they make it possible to measure the activation of one or the other of the intracellular signaling pathways via the same membrane receptor, which in this case is overexpressed by the cell, by conventional molecular biology techniques.

Study of a Cell Signaling Cascade.

The transmission of the signal inside the cell most commonly uses cascades of biological events. The methods according to the invention, by allowing the detection of these events in the same cell or the same population of cells, provide information which is much more complete than those which measure only a single event: by demonstrating the activation of at least two events known to be involved in a signaling cascade, it becomes possible to very precisely characterize the method of action of a given compound. This is particularly advantageous when one of the biological events has several effects in the cell.

By way of nonlimiting example, the phosphorylation cascades in the MAP kinase signaling pathway may be mentioned.

"Deorphaning" "Orphan" Receptors: Associating a G Protein-Coupled Receptor (GPCR) with a Ligand and with a Signaling Pathway.

A certain number of membrane receptors have been identified since the advent of the mass sequencing of genomes, in particular of the human genome. Nevertheless, for approximately 150 of said receptors, no natural ligand has been identified and these receptors are referred to as "orphan receptors". The methods according to the invention, on the one hand, facilitate the identification of orphan-receptor ligands and, on the other hand, make it possible to determine the intracellular signaling pathways activated by an orphan receptor.

The conventional method for "deorphaning" such receptors, i.e. for identifying the natural ligand(s) thereof, consists in making cells overexpress said receptor and in adding to the culture medium a compound for which it is desired to know whether it is a natural ligand for said receptor. The binding of the potential ligand can be easily measured by techniques known to those skilled in the art.

The methods according to the invention make it possible to apply this approach to the simultaneous "deorphaning" of several orphan receptors; these methods in fact make it possible to individually detect the binding of a ligand to various membrane receptors expressed on the same cell or cell population: for this particular application of the methods according to the invention, each of the pairs of FRET partner conjugates will make it possible to detect the binding of the same potential ligand with the various orphan receptors. In this case, the molecules involved in the biological event are, on the one hand, a potential ligand and, on the other hand, various orphan receptors. The biological events consist of the potential binding of the ligand to each of the orphan receptors. Insofar as the same potential ligand is involved in various biological events, it is particularly advantageous, in this precise application, for the pairs of FRET partners to have a common element, in the case in point the conjugate comprising or recognizing the ligand.

Another approach aimed at deorphaning a receptor consists in measuring the activation of various intracellular signaling pathways by means of a method according to the invention as described above, after cells overexpressing an orphan receptor have been brought into contact with a potential ligand of said receptor, this ligand being introduced into the reaction medium during a stimulation step: this type of approach makes it possible to associate a potential ligand, an orphan receptor and a signaling pathway.

Normalization of Two Biological Events with Respect to One Another, in Particular Detection of a Substrate in Modified Form and of the Total Substrate, in the Same Medium.

The methods according to the invention also make it possible to normalize, with respect to one another, two signals corresponding to two given biological events taking place in the same reaction medium. This is particularly advantageous in the case where one of the biological events is a change in the amount of a modified substrate—for example, through an enzyme—and the other biological event is a change in the total amount of this substrate (substrate modified by said enzyme+unmodified substrate). This type of normalization of the modified substrate relative to the total substrate makes it possible to overcome, to a certain extent, the variability in the experimental conditions from one reaction medium to the other.

By way of nonlimiting example, the methods according to the invention are thus applicable for studying the following enzyme modifications: mono ADP ribosylation; poly ADP ribosylation; acetylation; glutathionylation; O-glycosylation; N-glycosylation; methylation; nitration; phosphorylation; prenylation; sumoylation; ubiquitination; proteolysis; biotinylation and glutamylation.

In this implementation, one pair of FRET partner conjugates makes it possible to measure the modified substrate and a second pair of FRET partner conjugates makes it possible to measure the total substrate. Preferably, one of the FRET partner conjugates is common to both pairs of FRET partner conjugates.

The scheme of FIG. 2 illustrates, for example, the principle of detection of the phosphorylation state of a protein. The method is based on the use of two donor conjugates and a single acceptor conjugate. A FRET killer which specifically recognizes a part of one of the donor conjugates is used.

In a first step, the total protein is detected through the FRET between the donor $D_1$ and the acceptor A, carried by two antibodies which recognize the protein (signal $S_T$). In a second step, the signal $S_T$ generated by the total protein is quenched by a FRET killer (Fk) which specifically recognizes the donor $D_1$ and suppresses the FRET between $D_1$ and A. Simultaneously, the phosphorylated sites are recognized by a specific antibody which carries a second donor $D_2$. The FRET between $D_2$ and the acceptor A makes it possible to detect the phosphorylated proteins (signal $S_P$). This format is very suitable for screening for kinase inhibitors, for example. The detection of the amount of total protein and of the amount of phosphorylated protein makes it possible to correct the variations in cell number and/or in the amount of protein expressed in the various reaction volumes in the presence of the various test inhibitors (normalization procedure).

The invention also relates to a kit of parts for carrying out the method according to the invention: such a kit comprises at least the following elements, provided together or separately:
   at least two pairs of fluorescent FRET partner conjugates specific for biological events;
   at least one FRET signal killer.

A kit of parts according to the invention may also contain instructions describing a protocol for bringing the various pairs of fluorescent FRET partner conjugates into contact in the reaction medium, and also instructions for the sequential suppression of the FRET phenomena in the reaction medium by adding FRET signal killers.

Theoretical Formats:

The multiplexing method according to the invention may be carried out according to several formats:

(i) Format 1: specific recognition of a part of the donor conjugate by a FRET signal killer and suppression of the FRET;

(ii) Format 2: specific recognition of a part of the acceptor conjugate by a FRET signal killer and suppression of the FRET;

(iii) Format 3: specific recognition of a part of the acceptor conjugate by a FRET signal killer and suppression of the FRET signal.

(i) Format 1: Specific Recognition of a Part of the Donor Conjugate by a FRET Signal Killer and Suppression of the FRET The scheme of FIG. 3 illustrates an example of implementation of this multiplexing format for detecting two analytes X and Y. This format is based on the use of:
   two donors, $D_1$ and $D_2$, which can be excited by the same stimulus (for example, the same excitation light wavelength),
   an acceptor A common to both donors,
   and a FRET signal killer capable of specifically recognizing one of the two donors and of suppressing the FRET between this donor and the acceptor.

In a first step, the analyte X is detected via the FRET between the donor $D_1$ and the acceptor A, carried by two antibodies specific for the analyte X. In a second step, the Fk product specifically recognizes the donor $D_1$ and suppresses the FRET between $D_1$ and the acceptor A. The suppression of the FRET quenches the signal generated by the presence of the analyte X. Simultaneously, the analyte Y is detected by the FRET between the donor $D_2$ and the acceptor A, carried by two antibodies specific for the analyte Y. This format is used in example 2.

(ii) Format 2: Specific Recognition of a Part of the Acceptor Conjugate by a FRET Signal Killer and Suppression of the FRET The scheme of FIG. 4 illustrates an example of implementation of this multiplexing format for detecting two analytes X and Y. This format is based on the use of:
   two acceptors, $A_1$ and $A_2$, that can be detected at the same wavelength;

a donor D common to both acceptors;
and a FRET signal killer capable of specifically recognizing one of the two acceptors and of suppressing the FRET between the donor and this acceptor.

In a first step, the analyte X is detected via the FRET between the donor D and the acceptor $A_1$ carried by two antibodies specific to the analyte X. In a second step, the Fk product specifically recognizes the acceptor $A_1$ and suppresses the FRET between D and $A_1$. The suppression of the FRET quenches the signal generated by the presence of the analyte X. Simultaneously, the analyte Y is detected via the FRET between the donor D and the acceptor $A_2$, carried by two antibodies specific for the analyte Y. This format is illustrated by example 5.

(iii) Format 3: Specific Recognition of a Part of the Acceptor Conjugate by a FRET Killer and Suppression of the FRET Signal The scheme of FIG. 5 illustrates an example of implementation of this multiplexing format for detecting two analytes X and Y. This format is based on the use of:
two acceptors, $A_1$ and $A_2$, that can be detected at the same wavelength;
a donor D common to both acceptors;
and a FRET signal killer capable of specifically recognizing one of the two acceptors and of suppressing the FRET signal of this acceptor.

In a first step, the analyte X is detected via the FRET between the donor D and the acceptor $A_1$, carried by two antibodies specific for the analyte X. In a second step, the Fk product specifically recognizes the acceptor $A_1$ and suppresses the FRET signal of $A_1$. Simultaneously, the analyte Y is detected via the FRET between the donor D and the acceptor $A_2$, carried by two antibodies specific for the analyte Y.

The invention will be described in further detail by means of the exemplary illustrations hereinafter, in which reference is made to FIGS. 6A, 6B and 7-14, a brief description of which is given below, FIGS. 1 to 5 representing the schemes mentioned above.

The abbreviations used in these examples have the meanings below:

PS2-GST: denotes a fusion protein comprising the PS2 protein (described in particular in patent EP 345 315) and the GST (glutathione-S-transferase) protein. Such a fusion protein is produced according to conventional molecular biology techniques, for example using an expression system such as a plasmid comprising the nucleic acid sequence encoding this fusion protein. The PS2 and GST sequences are known.

TBP: denotes trisbipyridine cryptate.

TBP5COOH: denotes trisbipyridine cryptate pentaacid.

PBP4COOH: denotes pyridine-bispyridine cryptate tetraacid.

A647: denotes the fluorophore alexa647 from the company Molecular Probe.

XL665: crosslinked allophycocyanin, used as acceptor fluorophore, sold by CIS bio international.

D2: fluorescent acceptor compound having the same photophysical characteristics as XL665.

Cy5: cyanin 5, acceptor fluorophore sold by the company GE Healthcare.

In these examples, the following antibodies, which are specific for various known antigens and which were prepared using conventional techniques, were used:

GSS11 antibody: denotes a monoclonal antibody specific for the GST protein.

BC04 antibody: denotes a monoclonal antibody specific for the PS2 protein.

IPM3 antibody: denotes a monoclonal antibody specific for TNFα, different than the IPM2 antibody.

IPM2 antibody: denotes a monoclonal antibody specific for TNFα, different than the IPM3 antibody.

G211 antibody: denotes a monoclonal antibody specific for the amyloid peptide Aβ1-42.

13E9 antibody: denotes a monoclonal antibody specific for the amyloid peptide Aβ1-40.

1E8 antibody: denotes a monoclonal antibody which recognizes both the Aβ1-42 and 1-40 amyloid peptides.

Example 1

Figure 1:
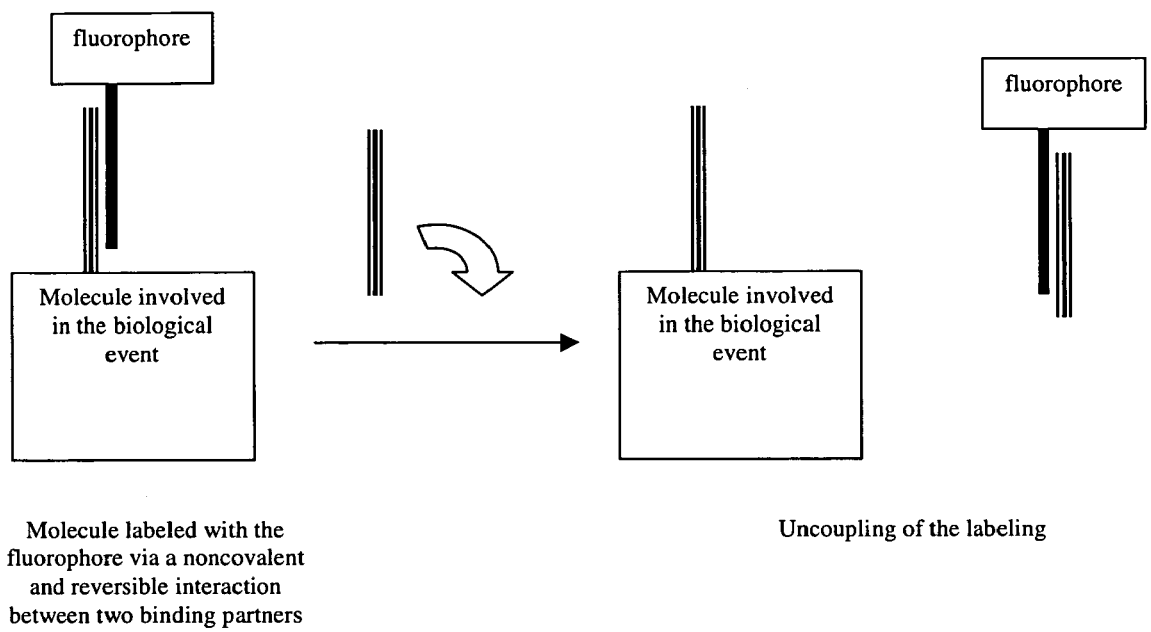
FIG. 1: scheme illustrating the competition phenomenon.
Figure 2:
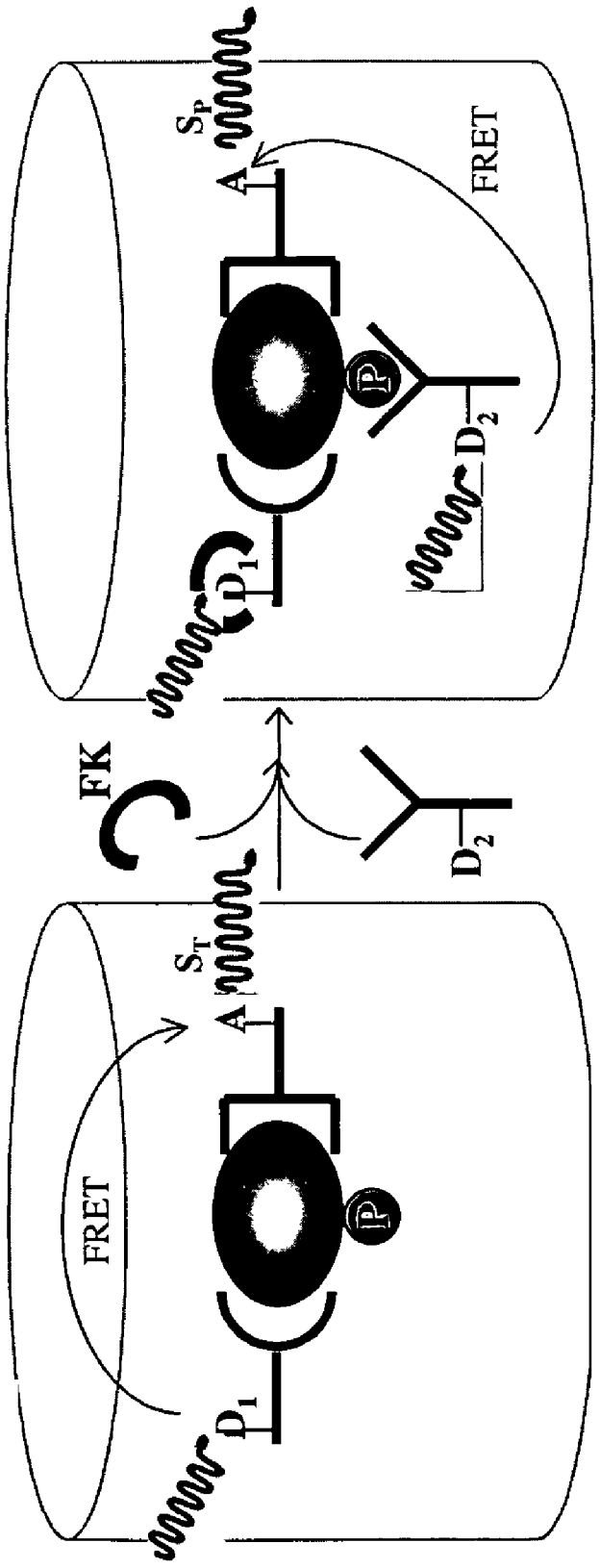
FIG. 2: scheme illustrating the principle of detection of the phosphorylation state of a protein.
Figure 3:
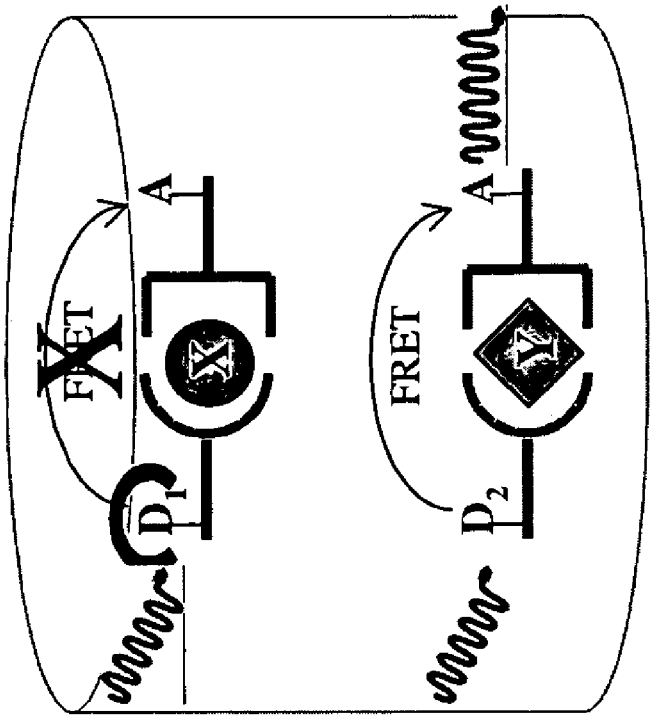
FIG. 3: scheme illustrating an exemplary embodiment of multiplexing format 1 for detecting two analytes X and Y.
Figure 3:
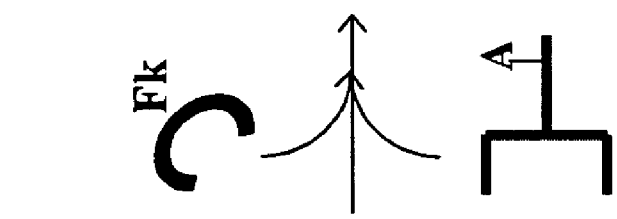
Figure 3:
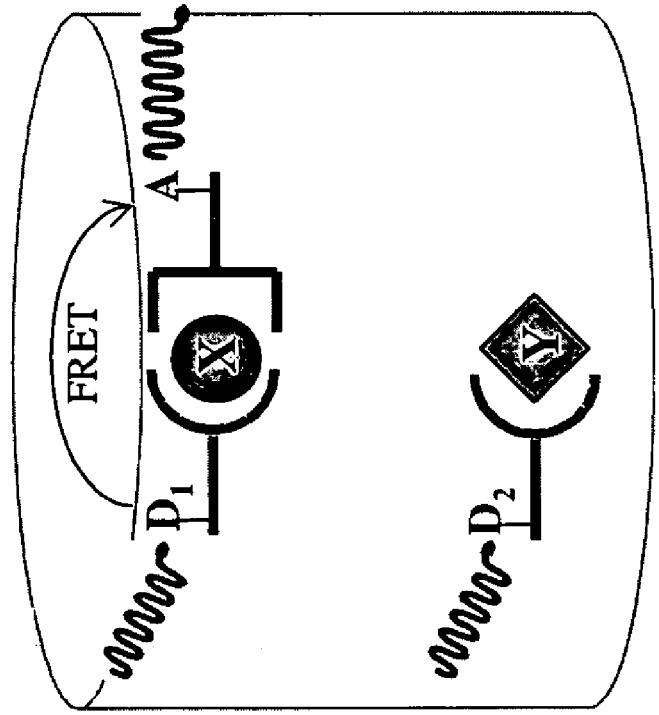
Figure 4:
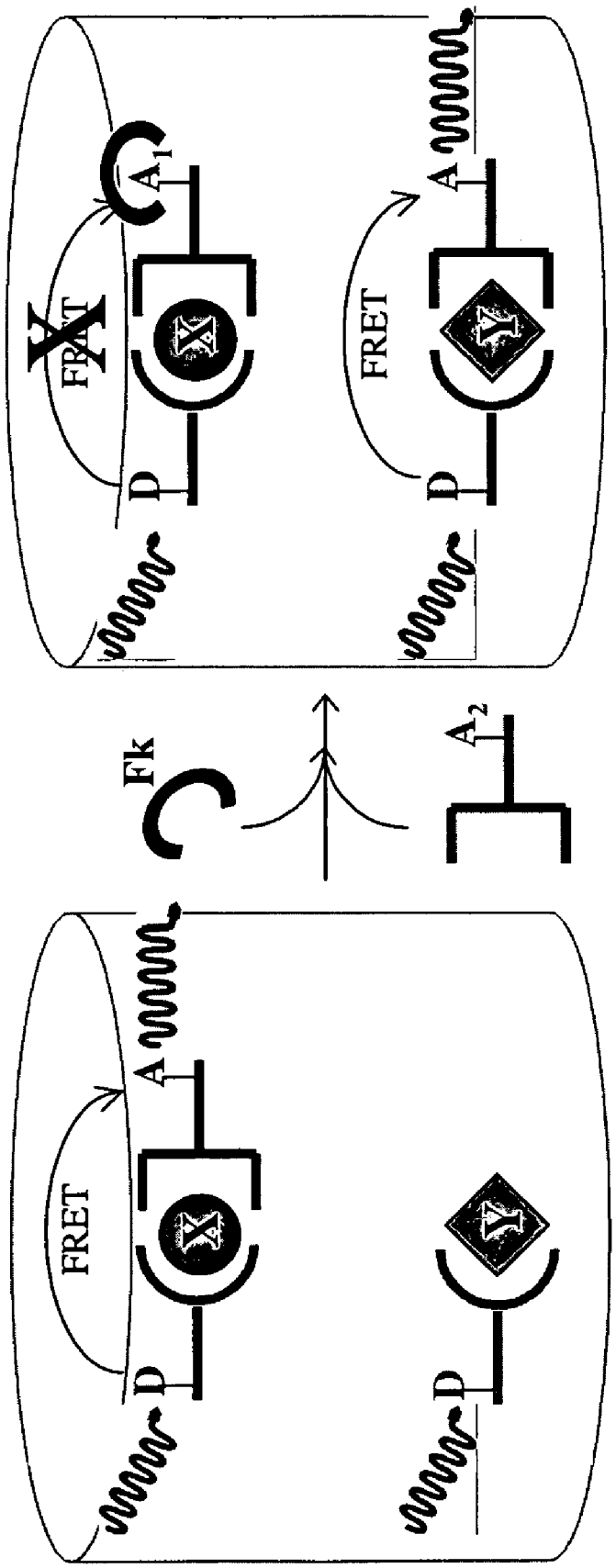
FIG. 4: scheme illustrating an exemplary embodiment of multiplexing format 2 for detecting two analytes X and Y.
Figure 5:
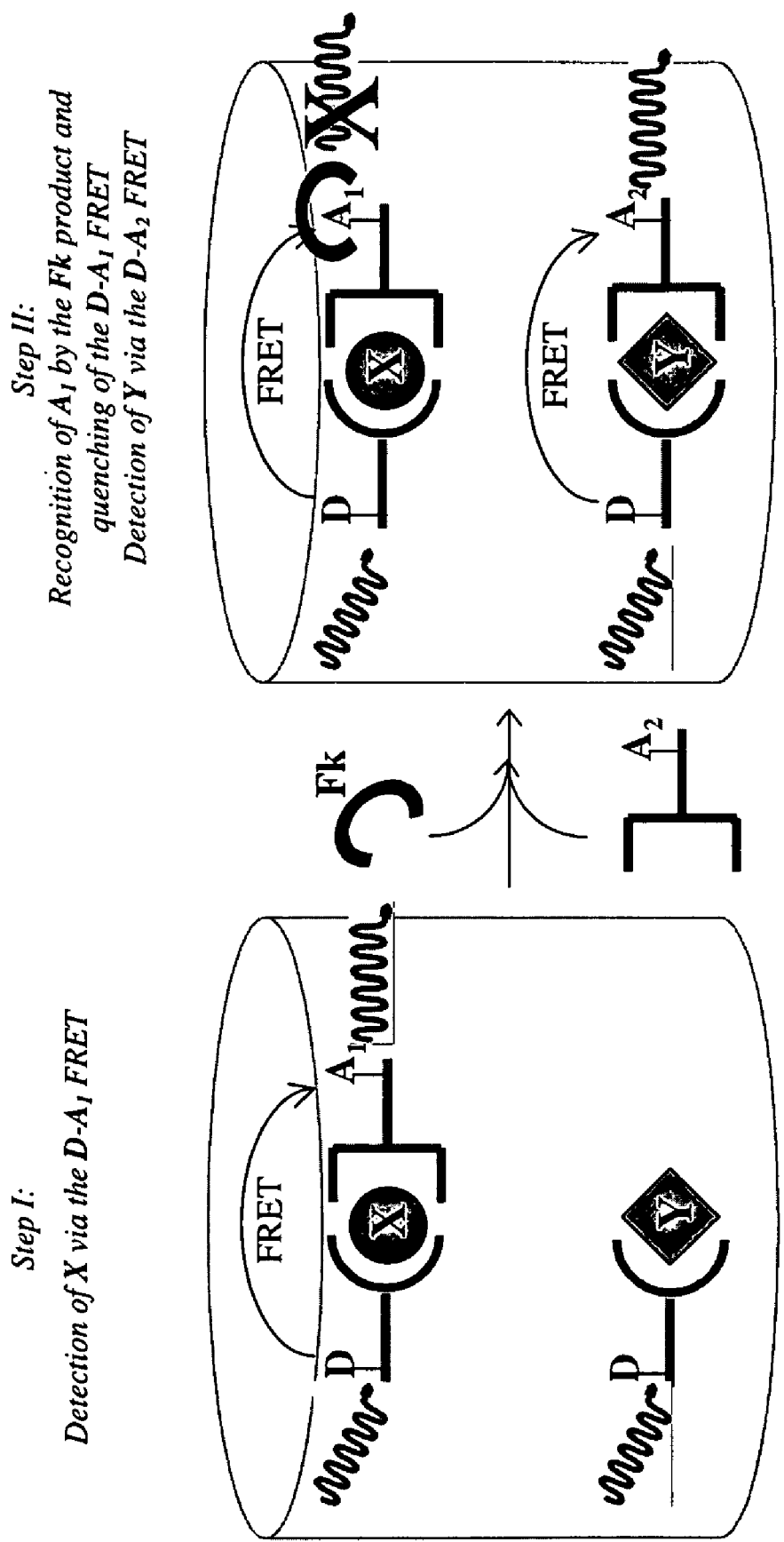
FIG. 5: scheme illustrating an exemplary embodiment of multiplexing format 3 for detecting two analytes X and Y.
Figure 6A:
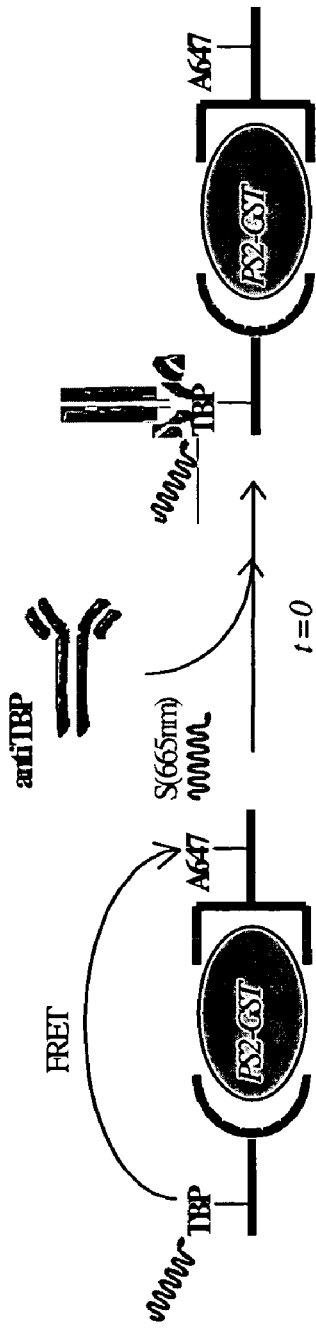
FIG. 6A: suppression of the FRET signal with an anti-cryptate antibody: after a step of detecting the PS2-GST protein via the FRET between the TBP and the acceptor A647 (graph I), increasing concentrations of anti-TBP were added to the reaction volume and the signal from the acceptor involved in the FRET was monitored over time (graph II. diamonds: 6 nM anti-TBP; triangles: 30 nM anti-TBP; squares: 150 nM anti-TBP). At suitable concentrations, the signal from the acceptor involved in the FRET disappears rapidly (<30 min). This quenching of the signal from the acceptor follows from the interaction between the TBP and the anti-TBP which suppresses the FRET.
Figure 6A:
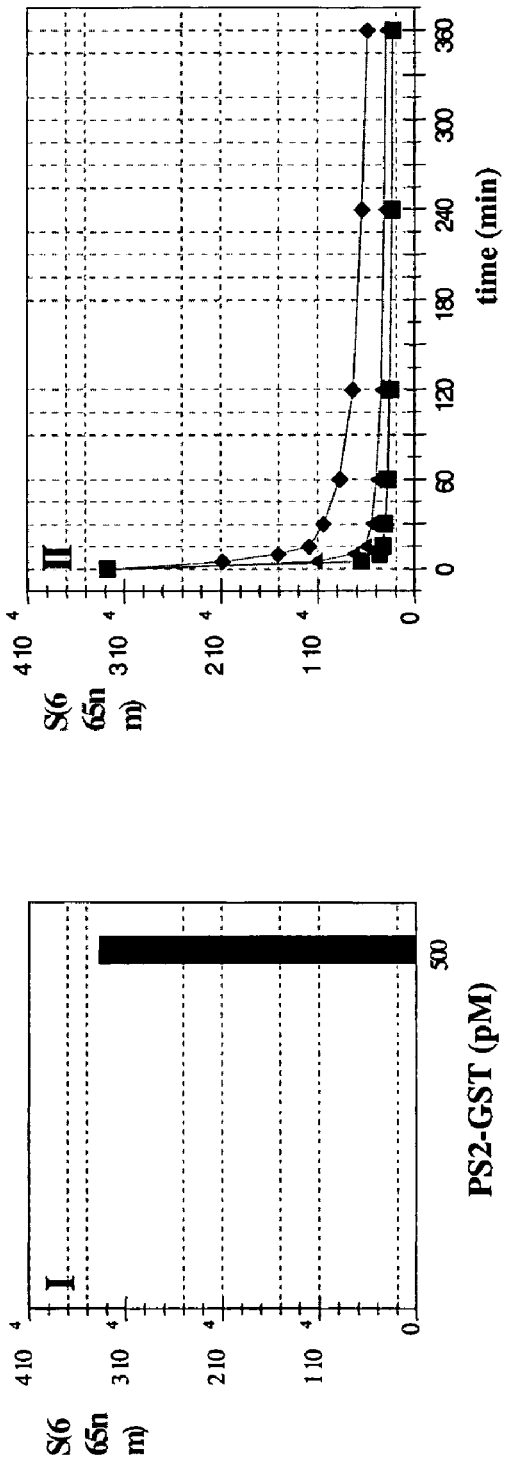
Figure 6B:
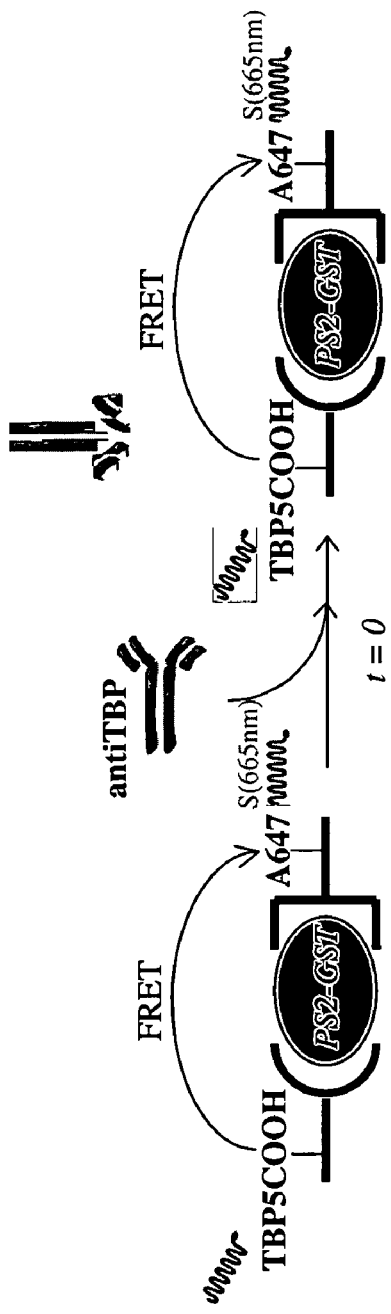
FIG. 6B: The same experiment as that presented in FIG. 6A was carried out using the donor TBP5COOH and the same acceptor A647. After having detected PS2-GST via the FRET between the TBP5COOH and the acceptor A647 (graph I), increasing concentrations of anti-TBP were added to the reaction volume and the signal from the acceptor involved in the FRET was monitored over time (graph II: circles: absence of anti-TBP; triangles: 6 nM anti-TBP; triangles: 30 nM anti-TBP; squares: 150 nM anti-TBP). The signal from the acceptor involved in the FRET does not decrease, whatever the concentration of anti-TBP.
Figure 6B:
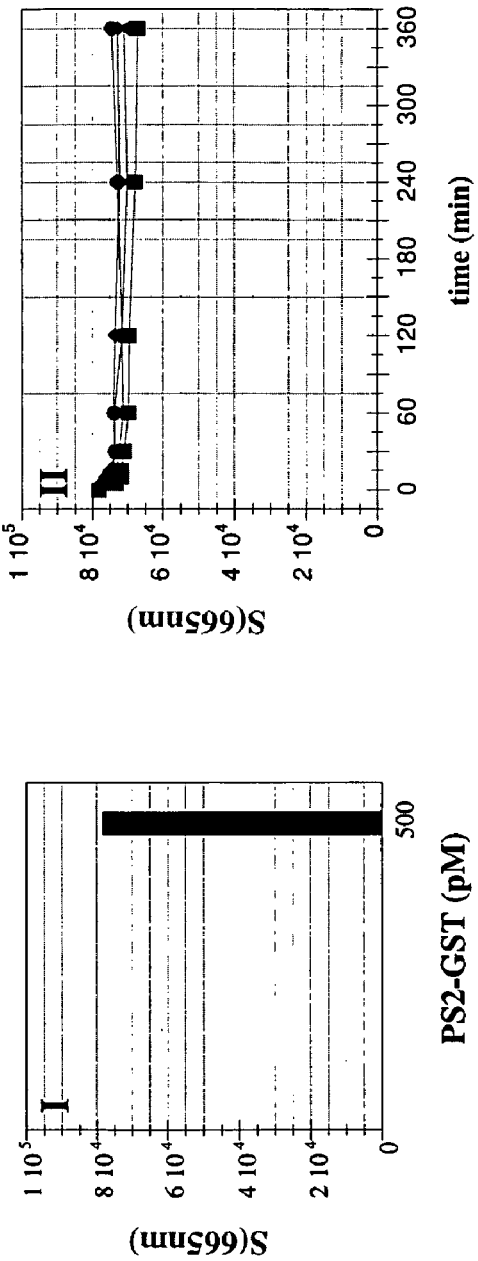

Suppression of the FRET Between a Donor and an Acceptor by a FRET Signal Killer which Specifically Recognizes a Part of the Donor Conjugate (FIGS. 6A and 6B)

An antibody which specifically recognizes a rare earth complex, europium trisbipyridine cryptate TBP, was produced according to conventional techniques (anti-TBP antibody). In this example, it is demonstrated that the anti-TBP specifically recognizes the europium cryptate TBP and suppresses the FRET between the TBP and its acceptor.

Protocol

Two identical experiments aimed at detecting a PS2-GST fusion protein were carried out. In each of the experiments, a particular europium cryptate structure was used as FRET donor: either trisbipyridine cryptate TBP or tris-bipyridine cryptate pentaacid TBP5COOH having the formulae below:

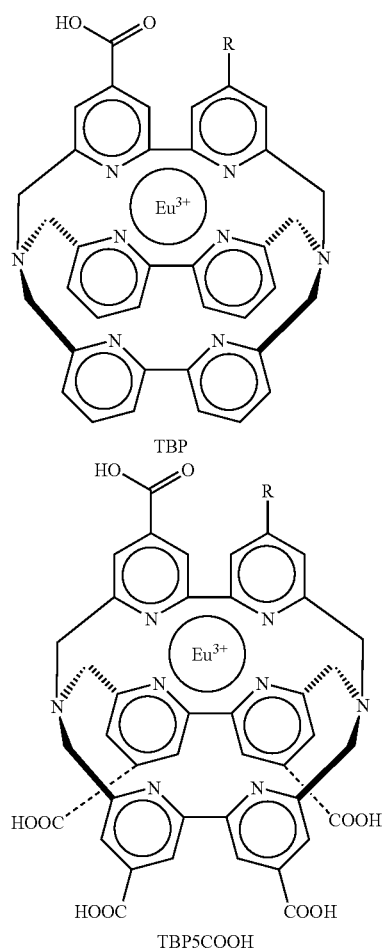

R is a conventional reaction group which allows the coupling of the cryptate with the substance to be labeled.

These two experiments are illustrated in FIGS. 6A and 6B.

The PS2-GST fusion protein is distributed into 96-well plates. Its presence is detected by FRET between the donor (TBP or TBP5COOH) (carried by the GSS11 antibody) and the acceptor A647 (carried by the BC04 antibody), after incubation for 16 h at ambient temperature. The signal emitted by the acceptor involved in the FRET (i.e. the signal from the acceptor following selective excitation of the donor) is termed S (665 nm).

Increasing concentrations of anti-TBP are subsequently added at time t=0 and the signal S (665 nm) from the acceptor involved in the FRET was monitored over time (ambient temperature, ≈20° C.).

Final concentrations:
500 μM PS2-GST; 1.5 nM GSS11; 0.677 nM BC04;
0.6 nM, 30 nM and 150 nM anti-TBP
Final reaction volume: 200 μl
Buffer: 100 mM phosphate, pH 7.0, 400 mM KF, 0.10% BSA
The signals were detected on a Rubystar (BMG Labtechnologies, excitation laser 337 nm).

Results

FIG. 6A illustrates the results of the experiment carried out with TBP. The protein to be detected (PS2-GST) is recognized by two specific antibodies carrying the TBP donor and the A647 acceptor. Following recognition of the protein by the two antibodies, the TBP and its acceptor are in proximity. When the TBP is selectively excited (337 nm), its excitation energy is then in part transferred to the acceptor by FRET. This energy transfer causes an emission of fluorescence from the acceptor (the signal S (665 nm)). The appearance of the emission from the acceptor following the selective excitation of the donor makes it possible to detect the protein.

After having thus detected the protein (FIG. 6A, graph I), the anti-TBP antibody is added, at time t=0, to the reaction volume. Quenching of the signal S (665 nm), i.e. of the signal from the acceptor involved in the FRET (FIG. 6A, graph II), is then observed.

The quenching of this signal is not due to interaction of the anti-TBP with the acceptor used, but follows only from the suppression of the FRET following the specific interaction of the anti-TBP with the TBP. In order to prove this, the same experiment was carried out using a different donor (TBP5COOH in place of TBP), and the same acceptor A647 (FIG. 6B). The FRET between the TBP5COOH and the A647 makes it possible to detect the protein (FIG. 6B, graph I). The presence of the anti-TBP does not modify this FRET: the signal S (665 nm) does not decrease, whatever the concentration of anti-TBP (FIG. 6B, graph II). The disappearance of the signal from the acceptor observed with the TBP (FIG. 6A, graph II) is therefore indeed due to the suppression of the FRET between the TBP donor and the acceptor following the specific recognition of the TBP by the anti-TBP.

Example 2

Figure 7:
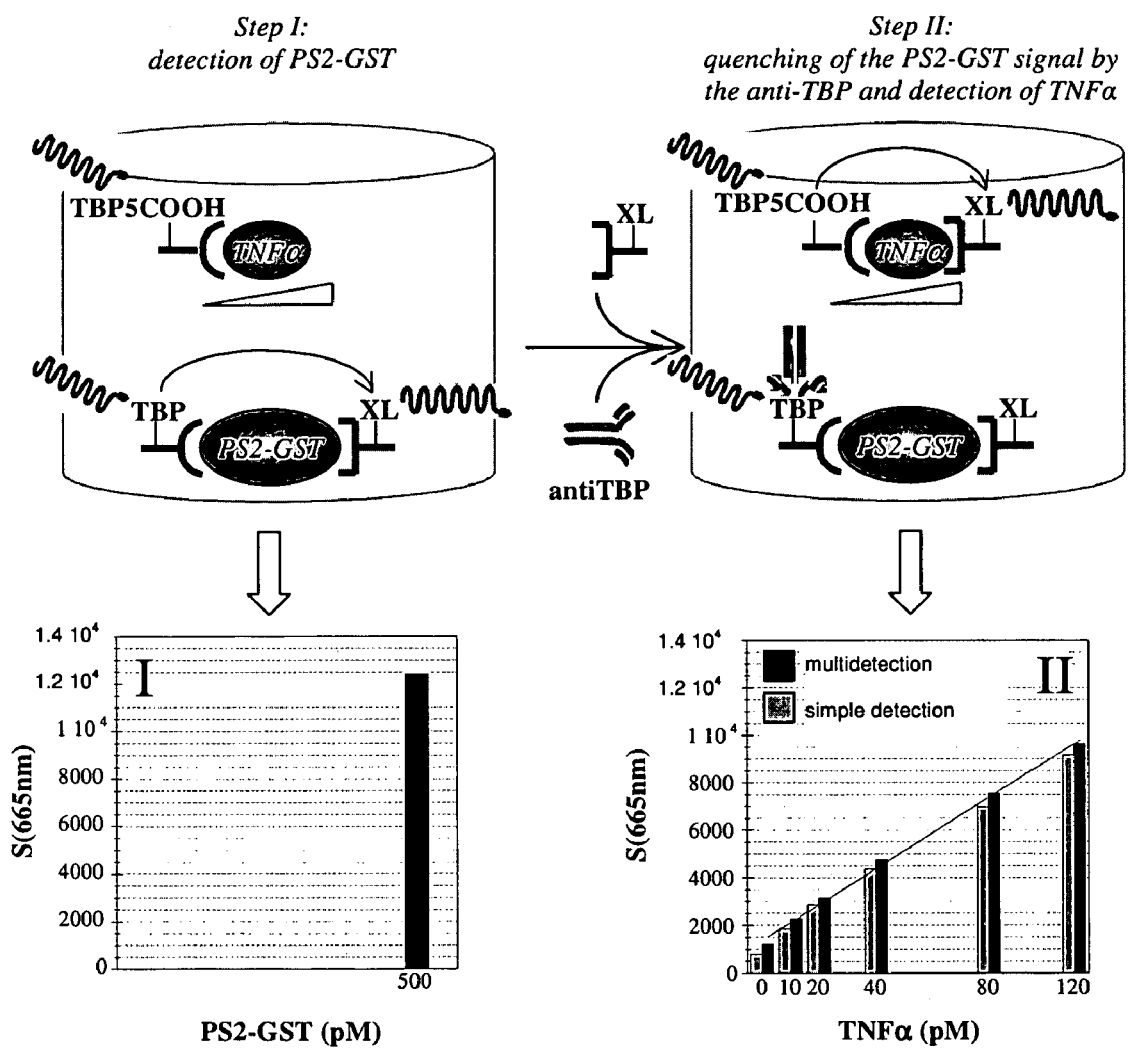
FIG. 7: Example of multidetection of two proteins by recognition of a donor and suppression of the FRET: after a step of detecting the PS2-GST protein by the FRET between the TBP and the acceptor XL665 (graph I), the anti-TBP and the second antibody for detecting TNFα are added. The anti-TBP specifically recognizes the TBP, suppresses the FRET between the TBP and the XL665 and thus quenches the signal from the PS2-GST. Simultaneously, the TNFα is detected via the FRET between the TBP5COOH and the XL665 (graph II, dark bars), carried by two antibodies specific for TNFα. The signals obtained in the multidetection assay (graph II, dark bars) are comparable to those obtained in a simple detection assay (graph II, light gray bars).

Multiplexed Detection of Two Proteins, PS2-GST and TNFα—Suppression of FRET by an Agent Binding to One of the Donor Fluorophores (FIG. 7)

This example is based on the use of two donors that can be excited at the same wavelength (TBP and TBP5COOH) and a single common acceptor detectable at 665 nm (the fluorescent protein XL665). The FRET signal killer is the anti-TBP antibody, which specifically recognizes the TBP and suppresses the FRET between the TBP and its acceptor, as is shown in the previous example.

Protocol

The experiment is illustrated in FIG. 7, for the detection of two analytes: the PS2-GST protein and the TNFα protein. A range of TNFα concentrations was measured, after a first step of detecting the PS2-GST protein and quenching of the corresponding FRET signal.

Multiplexing Experiment

A range of concentrations of TNFα in the presence of a fixed concentration of PS2-GST is dispensed in a 96-well plate.

The PS2-GST protein is first of all detected by FRET between the europium cryptate TBP (carried by the GSS11 antibody) and the XL665 acceptor (carried by the BC04 antibody), after incubation for 16 h at ambient temperature.

The following compounds are subsequently added to the reaction volumes:
the anti-TBP, in order to suppress the FRET between the TBP and the XL665 and therefore the signal due to the presence of the PS2-GST protein;
and the second antibody, in order to detect the TNFα protein: the IPM3 antibody carrying the XL665 acceptor (the IPM2 antibody carrying the europium cryptate TBP5COOH donor being distributed in step I).

After incubation for 4 h at ambient temperature (so as to allow recognition of the TNFα by the specific IPM3 antibody), the signals obtained in the wells containing the various concentrations of TNFα are measured.

Control Experiment: Simple Detection

The signals thus obtained in the multiplexing assay are compared with the signals obtained in a simple assay for detecting TNFα (i.e. the same experiment illustrated in FIG. 7, but in the absence of PS2-GST).

Final concentrations of the proteins and of the antibodies:
500 pM PS2-GST; 1.5 nM GSS11; 0.667 nM BC04;
150 nM anti-TBP;
0, 10, 20, 40, 80 and 120 pM TNFα; 0.33 nM IPM2; 0.8 nM IPM3

Final reaction volume: 200 µl

Buffer: 100 mM phosphate, pH 7.0, 400 mM KF, 0.10% BSA

The signals were detected on a Rubystar (laser excitation 337 nm).

Results

In a first step, the PS2-GST protein was detected via the FRET between the TBP and the XL665 acceptor. The FRET signal S (665 nm), generated by the presence of the PS2-GST protein, is represented by the bar of histogram I, FIG. 7. In a second step, the anti-TBP antibody for suppressing the FRET due to the PS2-GST protein and the second antibody for detecting the TNFα were added to the reaction volumes. The signals detected after the addition of these compounds are represented by the dark bars of histogram II, FIG. 7.

A control experiment made it possible to validate this multiplexing experiment: the results obtained by multiplexing are compared with those obtained in a simple detection assay. More specifically, the same experiment as that illustrated in the scheme of FIG. 7 was carried out, but in the absence of the PS2-GST protein. In this simple detection assay, there is no signal to be quenched and the various TNFα concentrations are detected directly. The signals obtained are represented by the light bars of histogram II, FIG. 7. The signals derived from the multiplexing are comparable to those derived from the simple detection.

Example 3

Figure 8:
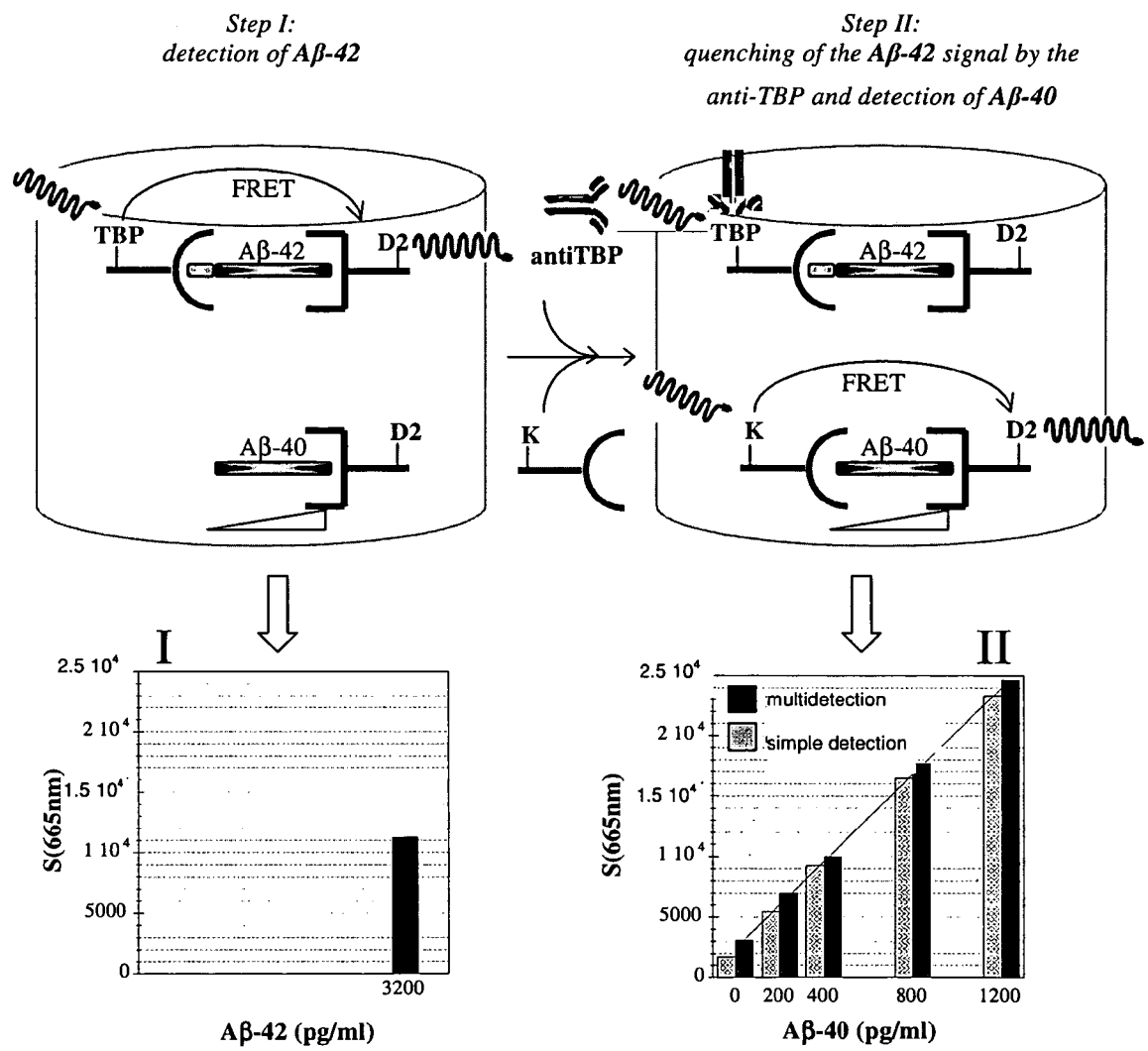
FIG. 8: Example of multidetection of the amyloid peptides Aβ-40 and Aβ-42 by recognition of a donor and suppression of the FRET: after a step of detecting the Aβ-42 peptide via the FRET between the TBP and the acceptor D2 (graph I), the anti-TBP and the antibody for specifically detecting the Aβ-40 are added. The anti-TBP specifically recognizes the TBP, suppresses the FRET between the TBP and D2, and thus quenches the signal from the Aβ-42. Simultaneously, the Aβ-40 is detected by the FRET between another type of europium cryptate K (carried by an antibody specific for Aβ-40) and D2 (graph II, dark bars). The signals obtained in the multidetection assay (graph II, dark bars) are comparable to those obtained in a simple detection assay (graph II, light gray bars).

Multiplexed Detection of the Aβ-40 and Aβ-42 Amyloid Peptides—Suppression of FRET by an Agent which Recognizes One of the Donor Fluorophores (FIG. 8)

The Aβ-40 and Aβ-42 amyloid peptides are involved in Alzheimer's disease. In this disease, the production of the neurotoxic peptide Aβ-42 is favored compared with that of Aβ-40. The Aβ-42 peptide differs from the Aβ-40 peptide by virtue of the presence of two additional amino acids at one end. FIG. 8 illustrates the multiplexed detection of the Aβ-40 and Aβ-42 amyloid peptides. The experiment is based on the use:
of two donor conjugates (one conjugate for specific recognition of the Aβ-42 peptide and carrying a europium cryptate TBP, and one conjugate for specific recognition of the Aβ-40 peptide and carrying a different europium cryptate, TBP5COOH, also referred to hereinafter as europium cryptate K;
of a single acceptor conjugate which can recognize the two peptides Aβ-42 and Aβ-42;
and of the anti-TBP FRET signal killer.

Protocol

The experiment is illustrated in FIG. 8: an Aβ-40 peptide range was measured, after a step of detecting the Aβ-42 peptide and quenching of the corresponding FRET signal.

Multiplexing Experiment

A range of concentrations of Aβ-40 in the presence of a fixed concentration of Aβ-42 is dispensed into a 96-well plate. The two peptides are recognized by an antibody (1E8) carrying an acceptor (the d2 acceptor) common to the two donors used in this experiment. The Aβ-42 peptide is also recognized by a specific antibody (G211) carrying a europium cryptate TBP. After having thus detected the Aβ-42 peptide via the FRET between the TBP and the d2 acceptor, the following compounds are added to the reaction volumes:

the anti-TBP for suppressing the FRET between the TBP and the d2 acceptor and therefore the signal due to the presence of the Aβ-42;

and an antibody (13E9) for specifically detecting the Aβ-40; this antibody carrying the europium cryptate K which is not recognized by the anti-iTBP.

After incubation for 3 h at 4° C. (so as to allow recognition of the Aβ-40 by its antibody), the signals obtained are measured in the wells containing the various concentrations of Aβ-40.

Controlled Experiment: Simple Detection

The signals thus obtained in the multiplexing assay are compared with the signals obtained in a simple assay for detecting Aβ-40 (i.e. the same experiment as that illustrated by FIG. 8, but in the absence of the Aβ-42 peptide).

Final concentrations of the peptides and of the antibodies:
3200 pg/ml A#42;
200, 400, 800 and 1200 pg/ml Aβ-40;
3.3 nM 1E8; 0.8 nM G211; 0.34 nM 13E9
Final reaction volume: 100 µl
Buffer: 50 mM phosphate, pH 7.4, 250 mM KF, 0.20% BSA, 0.050% Tween, 0.25 mM EDTA The signals were detected on a Rubystar (laser excitation 337 nm).

Results

In a first step, the Aβ-42 peptide is detected via the FRET between the TBP and the d2 acceptor. The d2 acceptor is carried by an antibody which recognizes the two peptides, while the TBP donor is carried by an antibody which specifically recognizes the Aβ-42 peptide. The signal S (665 nm) from the acceptor involved in the FRET is represented by the bar of histogram I, FIG. 8.

In a second step, the anti-TBP (for suppressing the signal due to the Aβ-42 peptide) and an antibody which specifically recognizes the Aβ-40 peptide and which carries the europium cryptate K different than TBP were added to the reaction volumes. The signals detected after the addition of these compounds are represented by the dark bars of histogram II, FIG. 8.

In order to validate the signals obtained in this multiplexing experiment, the same experiment as that illustrated in FIG. 8 was carried out, but in the absence of the Aβ-42 peptide. In this simple detection assay, there is no signal to be quenched and the various concentrations of Aβ-40 are detected directly. The signals obtained are represented by the light bars of histogram II, FIG. 8. The signals derived from the multiplexing are comparable to those derived from the simple detection.

Example 4

Figure 9:
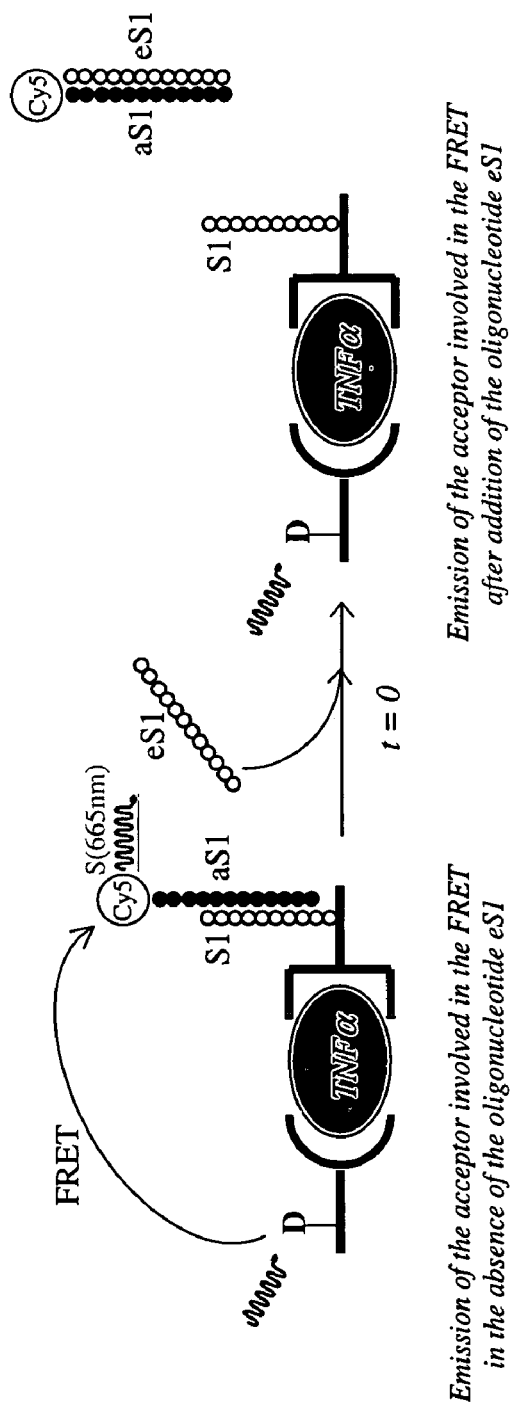
FIG. 9: After a step of detecting TNFα via the FRET between a europium cryptate donor and the acceptor probe aS1-Cy5 (graph I), increasing concentrations of oligonucleotide eS1 were added to the reaction volume and the signal from the acceptor involved in the FRET was monitored over time (graph II: circles: 8 nM eS1; diamonds: 20 nM eS1; triangles: 100 nM eS1; squares: 200 nM eS1). The oligonucleotides aS1 and eS1 are complementary. The final concentrations of eS1 and of aS1-Cy5 are 2 nM and 4 nM, respectively. At suitable concentrations, the signal from the acceptor involved in the FRET disappears completely and rapidly (<30 min).
Figure 9:
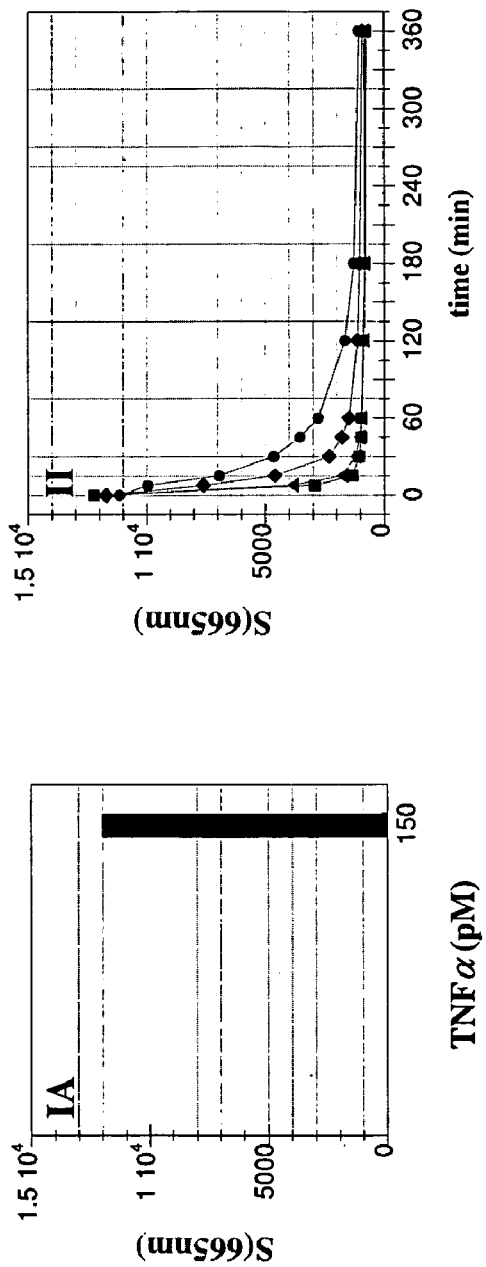

Suppression of the FRET Between a Donor and an Acceptor by a FRET Signal Killer which Acts by Uncoupling the Acceptor Fluorophore (FIG. 9)

This example relates to a FRET signal killer which acts by forming a noncovalent complex with one of the FRET partner conjugates, and will uncouple it from the biological event for which it is specific, by a competition mechanism.

Nature and Mode of Action of this Fret Signal Killer

This FRET signal killer is an oligonucleotide. FIG. 9 illustrates its mode of action.

In this example, the fluorescent acceptor conjugate consists of a small fluorescent organic molecule (a cyanin Cy5) coupled to an oligonucleotide of sequence aS1. This sequence hybridizes to a complementary sequence S1 coupled to an antibody specific for the protein to be detected.

After having detected the biological event via the FRET between a donor conjugate and an acceptor conjugate, an oligonucleotide eS1 having a sequence complementary to aS1 is added to the reaction volume. The eS1 sequence specifically recognizes the aS1 sequence and thus displaces the fluorescent acceptor conjugate (aS1-Cy5) of the antibody specific for the protein to be detected. The displacement of the fluorescent acceptor conjugate suppresses the FRET between the donor conjugate and the acceptor conjugate.

The oligonucleotide eS1 constitutes an example of a FRET signal killer which specifically recognizes a part of the acceptor conjugate and suppresses the FRET. The specificity of recognition is based, in this case, on the pairing of two complementary DNA sequences.

Protocol

The TNFα protein was dispensed into a 96-well plate. Its presence was detected by FRET between a europium cryptate donor (carried by the IPM2 antibody) and the acceptor conjugate aS1-Cy5 (which binds to the IPM3 antibody by pairing of the complementary strands, as specified above). S (665 nm) is the signal from the acceptor involved in the FRET.

After having detected the protein, increasing concentrations of oligonucleotide eS1 were introduced at time t=0 and the signal S (665 nm) from the acceptor involved in the FRET was monitored over time (ambient temperature).

Final protein and antibody concentrations:
150 pM TNFα; 0.33 nM IPM2; 1.07 nM IPM3.

Final oligonucleotide concentrations:
2 nM S1; 4 nM aS1-Cy5; 8, 20, 100 and 200 nM eS1

```
Sequences:
S1   3'TTGATTTCGACAATTGTT5'          (SEQ ID NO: 3)

aS1  5'AACTAACGCTGGTAACAAGTCGTAC3'   (SEQ ID NO: 4)

eS1  3'TTgATtGCgACCATtGTTCAgCATG5'   (SEQ ID NO: 5)
the nucleotides in lower case characters are LNAs
(Locked Nucleic Acids)
```

Final reaction volume: 200 µl

Buffer: 50 mM HEPES, pH 7.0, 400 mM KF, 0.1% BSA; ambient temperature

The signals were detected on a Rubystar (laser excitation 337 nm).

Results

The hybridization between the aS1-Cy5 acceptor conjugate and the S1 sequence carried by the antibody makes it possible to detect the protein by FRET (FIG. 9, graph I). After having thus detected the protein, the eS1 product is added to the reaction volume. In the presence of the eS1 product, quenching of the signal S (665 nm) from the acceptor conjugate involved in the FRET (FIG. 9, graph II) is then observed. The quenching of this signal is due to the displacement of the aS1-Cy5 conjugate by eS1. The displacement of the acceptor conjugate suppresses the FRET between the donor and acceptor conjugates.

Example 5

Figure 10:
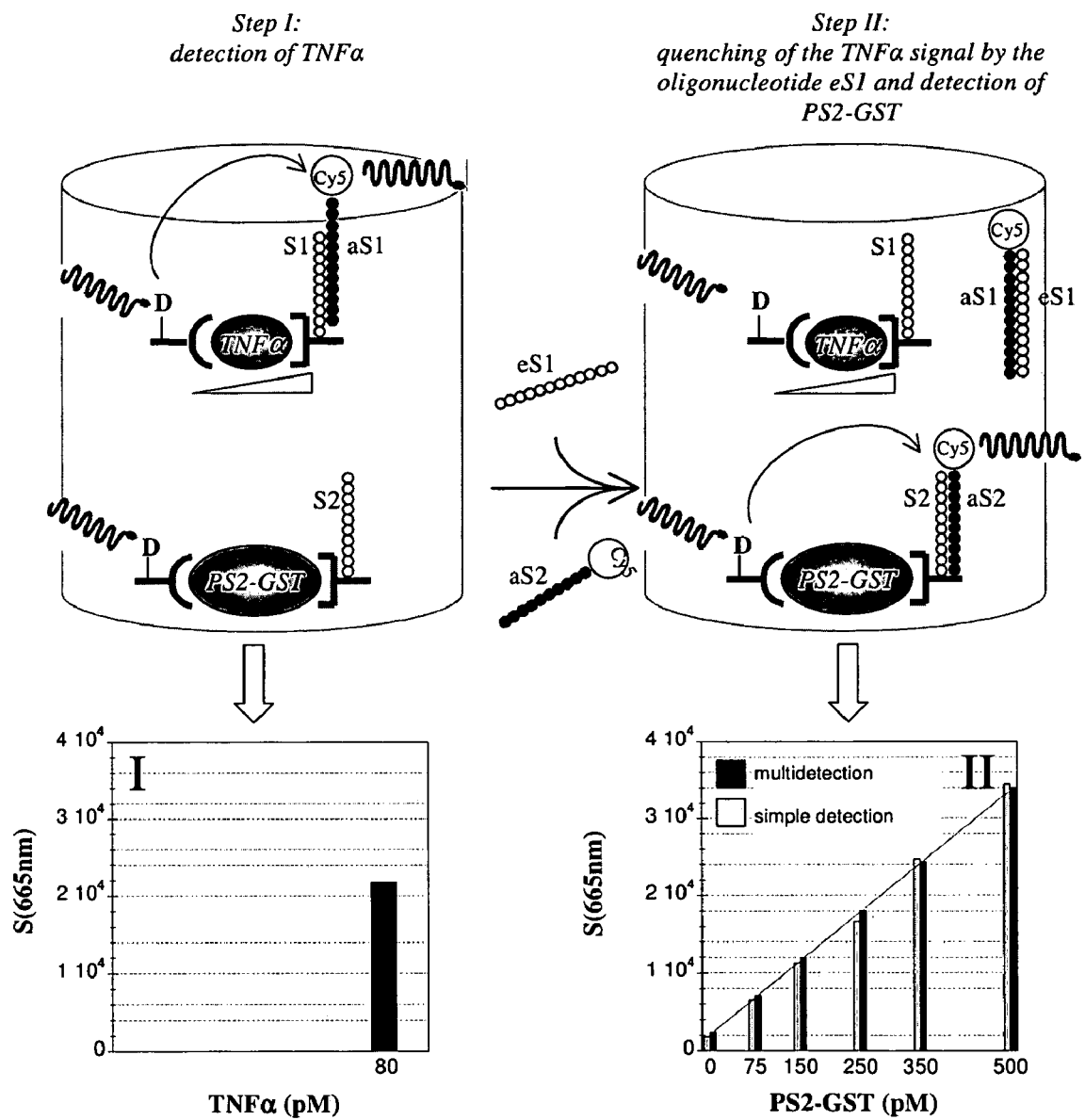
FIG. 10: Example of multidetection of two proteins by recognition of a part of the acceptor conjugate and suppression of the FRET. After a step of detecting TNFα by measuring the FRET (graph I), the products eS1 and aS2-Cy5 are added. The oligonucleotide eS1 specifically recognizes the sequence aS1 and uncouples the probe aS1-Cy5 from the anti-TNFα antibody, thus suppressing the FRET due to the presence of TNFα. Simultaneously, the probe aS2-Cy5 hybridizes to the sequence S2, which makes it possible to detect the PS2-GST protein. The signals obtained in the multidetection assay (graph II, dark bars), are similar to those obtained in a simple detection assay (graph II, light bars).

Multiplexed detection of two proteins, TNFα and PS2-GST—Suppression of FRET by uncoupling of one of the acceptor Fluorophores (FIG. 10)

This examples is based on the use of a single donor D (a europium cryptate) and two acceptor conjugates (aS1-Cy5 and aS2-Cy5). The acceptor conjugates consisting of a cyanin coupled to an oligonucleotide sequence aS1, on the one hand, and aS2, on the other hand. The FRET signal killer is an oligonucleotide which specifically recognizes a part of one of the acceptor conjugates and suppresses the FRET, according to the mode of action illustrated in the previous example.

Protocol

FIG. 10 illustrates the principle of the multidetection experiment, for detecting two proteins: TNFα and PS2-GST. A range of concentrations of PS2-GST was measured after a step of detecting the TNFα protein and quenching of the corresponding FRET signal.

Multiplexing Experiment

A PS2-GST concentration range is dispensed in a 96-well plate in the presence of a fixed concentration of TNFα.

For the detection of the first protein (TNFα), the following compounds are introduced into each well:
- an antibody (IPM2) carrying a europium cryptate donor;
- and a conjugate consisting of an antibody (IPM3) carrying an oligonucleotide S1. The acceptor conjugate consists of a Cy5 coupled to an oligonucleotide aS1 which hybridizes specifically with S1. Similarly, for the detection of the second protein (PS2-GST), we used:
- an antibody (GSS11) carrying a europium cryptate donor;
- and an acceptor conjugate consisting of an antibody (BC04) carrying an oligonucleotide S2. The acceptor conjugate consists of a Cy5 coupled to an oligonucleotide aS2 which hybridizes specifically with S2.

In a first step, all the antibodies and also the aS1-Cy5 acceptor conjugate were dispensed into the wells. After incubation for 16 h at ambient temperature, the TNFα protein is detected by measuring the FRET signal emitted by each well.

In a second step, the following compounds were introduced into the wells:
- the oligonucleotide eS1, which has a sequence completely complementary to aS1,
- and the aS2-Cy5 acceptor conjugate.

The oligonucleotide eS1 hybridizes specifically with aS1 and thus displaces the aS1-Cy5 probe of the acceptor conjugate; the FRET no longer takes place and the signal from the TNFα protein therefore disappears. Simultaneously, the aS2-Cy5 probe hybridizes with S2 and makes it possible to "light up" the acceptor conjugate, i.e. to detect the PS2-GST protein.

Once the FRET signal killer eS1 and the aS2-Cy5 probe have been added, the FRET signals are measured after an incubation time of 30 minutes at ambient temperature.

Control Experiment: Simple Detection

The signals thus obtained in the multiplexing assay are compared with the signals obtained in a simple assay for detecting PS2-GST (i.e. the same experiment as that illustrated in FIG. 10, but in the absence of TNFα).

Final protein and antibody concentrations:
80 pM TNFα; 0.33 nM IPM2; 1.07 nM IPM3;
0, 75, 150, 250, 350 and 500 pM PS2-GST; 1 nM GSS11; 0.69 nM BC04.

Final oligonucleotide concentrations:
2 nM S1; 4 nM aS1-Cy5; 100 nM eS1
2 nM S2; 20 nM aS2-Cy5

Sequences:

```
Sequences:
S1   3'TTGATTTCGACAATTGTT5'         (SEQ ID NO: 3)

aS1  5'AACTAACGCTGGTAACAAGTCGTAC3'  (SEQ ID NO: 4)

eS1  3'TTgATtGCgACCATtGTTCAgCATG5'  (SEQ ID NO: 5)
the nucleotides in lower case characters are LNA
(Locked Nucleic Acids);

S2   3'ATATTGGTAGTTCCAGAT5'         (SEQ ID NO: 6)

aS2  5'TATAACCATCAAGGTCTA3'         (SEQ ID NO: 7)
```

Final reaction volume: 2000.
Buffer: 50 mM HEPES, pH 7.0, 400 mM KF, 0.1% BSA; ambient temperature.

The signals were detected on a RUBYstar (laser excitation 337 nm).

Results

In a first step, the TNFα protein is detected via the hybridization of the aS1-Cy5 probe with S1: the signal S (665 nm) from the aS1-Cy5 acceptor conjugate involved in the FRET is represented in histogram I, FIG. 10. The FRET signal killer oligonucleotide eS1 and the aS2-Cy5 acceptor conjugate are added in a second step. The signals detected after the addition of these products are represented by the dark bars of histogram II, FIG. 10.

In order to validate this multiplexing experiment, the signals thus obtained are compared with those obtained in a simple detection assay, i.e. an assay such as that illustrated in FIG. 10, but in the absence of the TNFα protein. In this simple detection assay, there is no signal to be quenched and the various concentrations of PS2-GST are directly detected. The signals of the simple detection assay are represented by the light bars of histogram II, FIG. 10: they are comparable with those obtained in the multidetection assay.

Example 6

Figure 11:
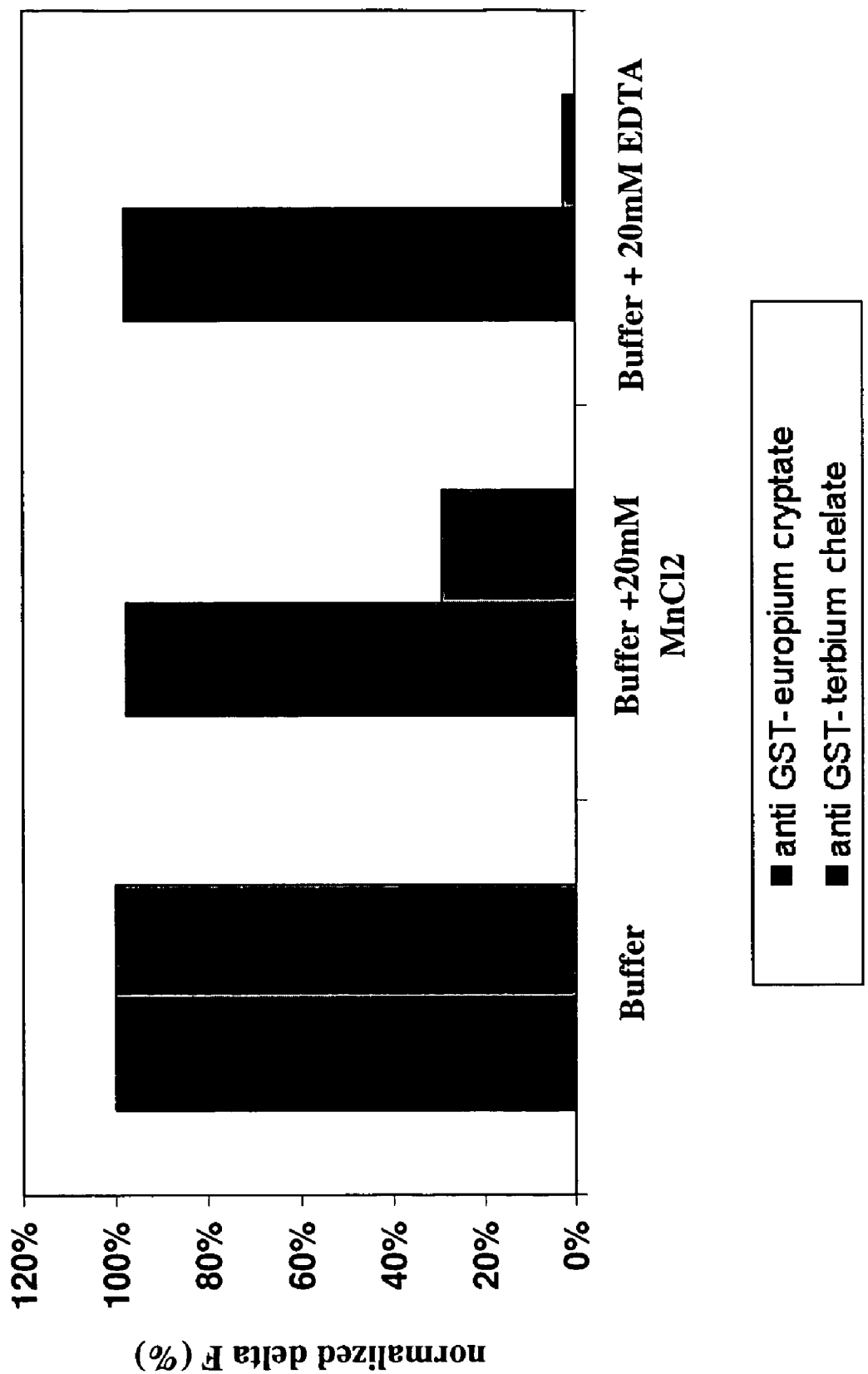
FIG. 11: Use of a divalent ion or of a chelating agent as FRET killer.

Use of a Divalent Ion or of a Chelating Agent as FRET Killer for the FRET Between a Donor and an Acceptor (FIG. 11)

In this example, it is demonstrated that the manganese ion or a chelating agent of EDTA type is capable of selectively suppressing the FRET existing between a donor of rare earth complex type and an acceptor.

Protocol

Two identical experiments aimed at detecting a GST-biotin protein were carried out. In each of the experiments, a particular rare earth complex was used as FRET donor: either the trisbipyridine cryptate TBP or a terbium chelate sold in a form conjugated to an anti-GST antibody by the company Invitrogen (Cat no. PV3568).

The biotinylated GST protein was dispensed into a 96-well plate. Its presence was detected by FRET between the donor (the TBP or the terbium chelate) (carried by an anti-GST antibody) and the d2 acceptor (carried by streptavidin), after incubation for 16 h at ambient temperature in the presence or absence of 20 mM of manganese chloride ($MnCl_2$) or of EDTA. A time-resolved fluorescence measurement is carried out (td=50 μs, tg=400 μs) at 620 nm and 665 nm (respectively E620 and E665) on a Rubystar® machine (BMG Labtech). Based on the fluorescence intensity values, E620 and E665, the E665/E620 intensity ratio is calculated and multiplied by 10 000 for greater convenience. The delta F values are calculated relative to the ratio measured in a negative well not containing the biotinylated GST (cf. G. Mathis, Clin. Chem. 39 (1993) 1953 and application WO92/13264). In order to compare the delta F values obtained in the various media for the same donor, said values are normalized relative to the delta F obtained in buffer (100%).

Final concentrations:
  1.25 nM biotinylated GST; 2 nM anti-GST; 5 nM streptavidin;
  20 mM $MnCl_2$ or EDTA
Final reaction volume: 200 µl
Buffer: 100 mM phosphate, pH 7.0, 400 mM KF, 0.10% BSA.
Results FIG. 11 illustrates the results obtained in the two experiments. The addition of 20 mM of $MnCl_2$ or of EDTA does not modify the FRET signal (normalized delta F) obtained with the TBP donor in the presence of biotinylated GST. Conversely, the $MnCl_2$ or the EDTA acts as a FRET killer (FRET signal inhibited by more than 70%) if the terbium chelate is used as donor for detecting the biotinylated GST. Since the rest of the assay components are identical, it may be concluded therefrom that these two FRET killers have acted selectively on the terbium chelate.

Example 7

Use of a Chemical Compound, Uric Acid, as FRET Killer for the FRET Between a Donor and an Acceptor In this example, it is demonstrated that uric acid is capable of selectively suppressing the FRET existing between a donor of rare earth complex type and an acceptor.

Protocol

Two identical experiments aimed at detecting a GST-biotin protein were carried out. In each of the experiments, a particular rare earth complex was used as FRET donor: either the trisbipyridine cryptate TBP or a pyridine-bis(bipyridine) cryptate PBP4COOH of formula:

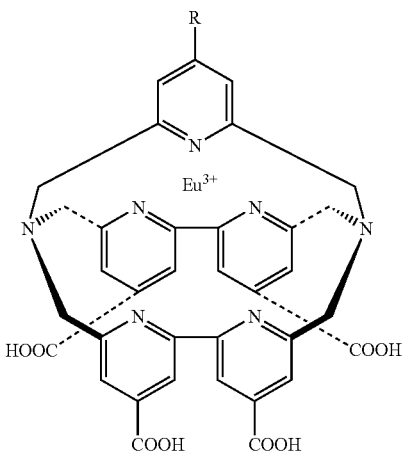

R is a conventional reaction group for coupling the cryptate with the substance to be labeled.

The biotinylated GST protein was dispensed into a 96-well plate. Its presence was detected via FRET between the donor (the TBP or PBP4COOH) (carried by the anti-GST antibody) and the d2 acceptor (carried by streptavidin), after incubation for 16 h at ambient temperature in the presence or absence of 60 µM of uric acid. A time-resolved fluorescence measurement (td=50 µs, tg=400 µs) is carried out at 620 nm and 665 nm (E620 and E665, respectively) on a Rubystar® machine (BMG Labtech). Based on the fluorescence intensity values, E620 and E665, the E665/E620 intensity ratio is calculated and multiplied by 10 000 for greater convenience. The delta F values are calculated relative to the ratio measured in a negative well not containing the biotinylated GST (cf G. Mathis, Clin. Chem. 39 (1993) 1953 and application WO92/13264). In order to compare the delta F values obtained in the various media for the same donor, said values are normalized relative to the delta F obtained in buffer (100%).

Figure 12:
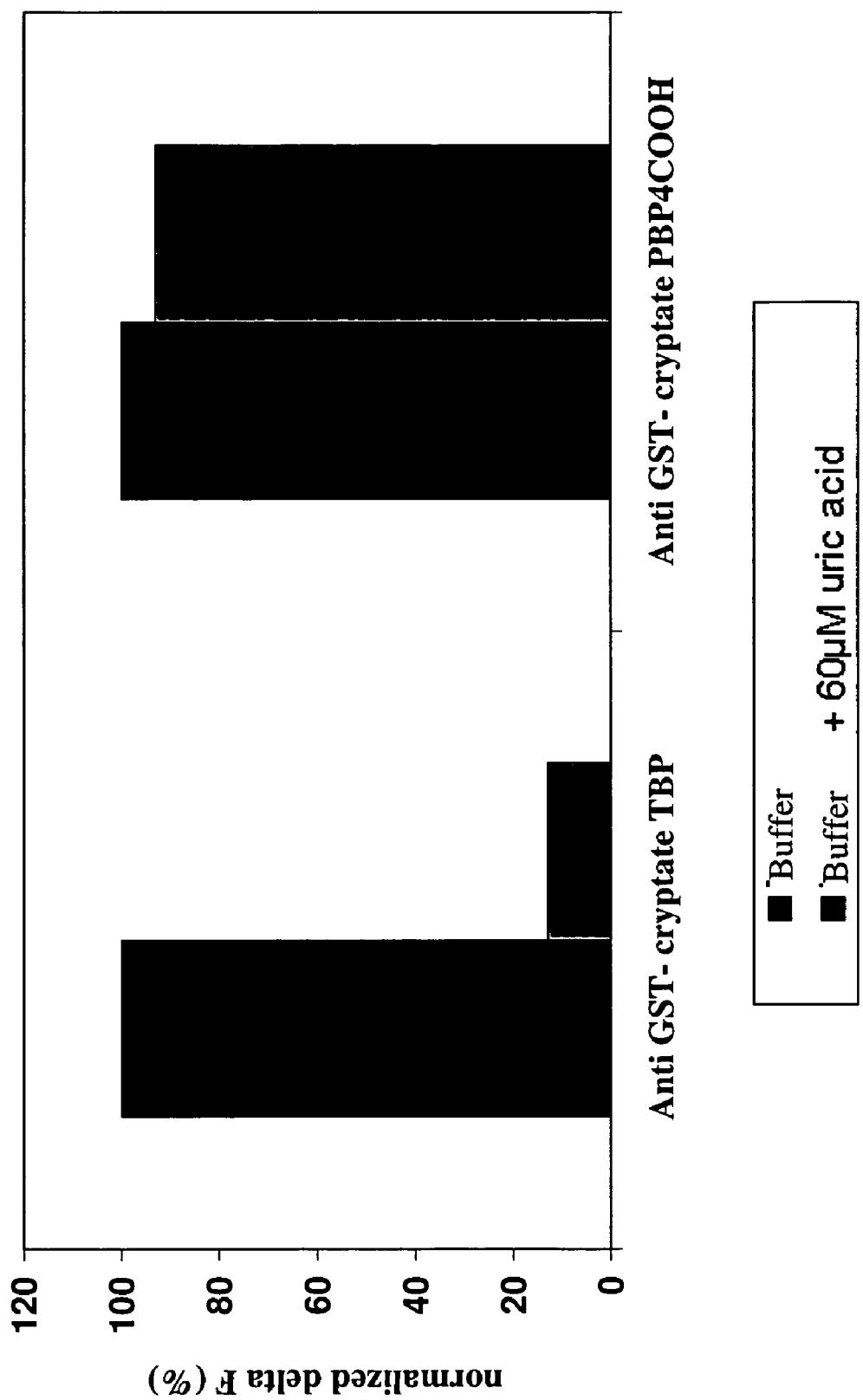
FIG. 12: Use of uric acid as FRET killer.

Final concentrations:
  1.25 nM biotinylated GST; 2 nM anti-GST; 5 nM streptavidin;
  60 µm uric acid.
Final reaction volume: 200 µl
Buffer: 100 mM phosphate, pH 7.0, 0.10% BSA.
Results FIG. 12 illustrates the results obtained in the two experiments. The addition of 60 µM of uric acid does not modify the FRET signal (normalized delta F) obtained with the PBP4COOH donor in the presence of biotinylated GST. Conversely, the uric acid acts as a FRET killer (FRET signal inhibited by more than 85%) if TBP is used as donor for detecting the biotinylated GST. Since the rest of the assay components are identical, it may be concluded therefrom that this FRET killer acts selectively on the europium cryptate TBP.

Example 8

Multiplexed Detection of the Intracellular Production of Second Messengers Following the Stimulation of a GPCR by an agonist Certain G protein-coupled receptors (GPCRs), such as the muscarinic receptor M1, may be coupled to various cell signaling pathways that can result in the production of specific second messengers, such as cAMP for the signaling pathway to Gαs proteins, or IP3 for the signaling pathway linked to Gαq proteins.

The activation of the M1 receptor by a specific agonist may thus induce an increase in the intracellular concentration of cAMP and of IP3. Since IP3 has a very short intracellular lifetime, the detection of the intracellular production thereof will be carried out indirectly by detecting its principal metabolite IP1 (Trinquet et al, "D-myo-inositol 1-phosphate as a surrogate of D-myo-inositol 1,4,5-tris phosphate to monitor G protein-coupled receptor activation" Analytical Biochemistry (2006) 358, 126-135).

This example describes the multiplexed detection, in the same microplate well, of the increase in the intracellular concentration of IP1 and of cAMP following activation of the M1 receptor by increasing doses of acetylcholine.

40 000 CHO-K1 cells expressing the M1 muscarinic acceptor, diluted beforehand in an RPMI culture medium containing 10% of fetal calf serum and a cocktail of antibiotics (volume 50 µl) are dispensed into each well of a 384-well white plate (Greiner, CellStar).

The plate is incubated for 20 h at 37° C. in an atmosphere containing 5% $CO_2$.

After the culture medium has been drawn off and the cells have been washed with 50 µl of KREBS/HEPES buffer, the cells are stimulated for 1 hour at 37° C. with 10 µl of a solution containing increasing concentrations of acetylcholine, diluted beforehand in a KREBS buffer containing 25 mM of LiCl, 1 mM of IBMX and 1% DMSO.

5 µl of a solution of an anti-IP1 antibody labeled with europium trisbipyridine cryptate (anti-IP1-TBP) at 4 nM and 5 µl of a solution containing 3 nM of an IP1 analog labeled with the d2 acceptor (IP1-d2) and 12 nM of a cAMP analog also labeled with the d2 acceptor are then added to each well. The solutions containing the labeled antibodies and analogs were prepared by diluting these molecules in a 0.1 M HEPES buffer, pH=7, +0.4M KF, 1% Triton X100 and 0.1% BSA. The addition of these reagents allows cell lysis and the detection of the intracellular production of IP1.

After incubation for one hour at ambient temperature, the IP1 production by the cells is detected by measuring the plate on a Rubystar reader (BMG Labtech). Each well is excited at 337 nm with a nitrogen laser, and the fluorescences emitted at 620 nm by the TBP and at 665 nm by the IP1-d2, following the process of nonradiative energy transfer (FRET) between the anti-IP1-TBP and the IP1-d2, are measured by time-resolved measurement (delay=50 µs; gate time=400 µs). The ratio of the fluorescence at 665 nm to the fluorescence at 620 nm is then calculated for each well using the following formula:

Ratio=(Fluorescence at 665 nm/Fluorescence at 620 nm)×10 000

Figure 13:
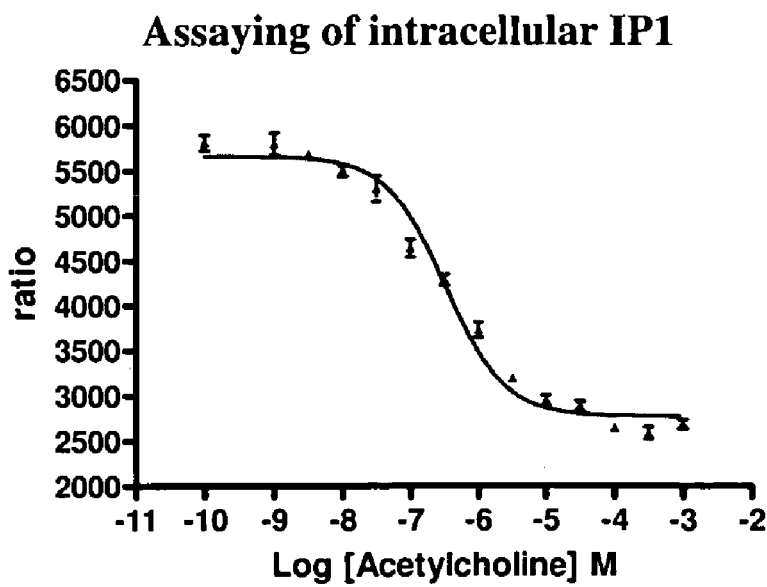
FIG. 13: Change in FRET signal representative of the amount of IP1 produced by the cell as a function of the concentration of acetylcholine present in the medium. The decrease in the FRET signal results from the production of IP1 by the cell, via a competition phenomenon (see example 8).

As shown in FIG. 13, as the intracellular IP1 production increases following stimulation of the M1 receptor with acetylcholine, the HTRF ratio decreases. This is because the IP1 produced by the cells competes with the IP1-d2 for binding the anti-IP1-TBP and thus decreases the FRET signal.

5 µl of a solution containing 0.92 nM of an anti-cAMP antibody labeled with europium cryptate 5COOH (anti-cAMP-TBP5COOH) and 0.12 mg/ml of an anti-anti-TBP monoclonal antibody (as FRET signal killer), diluted beforehand in a 0.1M HEPES buffer, pH 7, +0.4M KF+0.1% BSA, are then added to each well of the microplate. The addition of these reagents will make it possible to detect the intracellular production of cAMP.

After incubation for one hour at ambient temperature, the intracellular production of cAMP is detected by again measuring the plate on a Rubystar reader (BMG Labtech). Each well is excited at 337 nm with a nitrogen laser, and the fluorescences emitted at 620 nm by the TBP5COOH and at 665 nm by the cAMP-d2, following the FRET process between the anti-cAMP-TBP5COOH and the cAMP-d2, are measured by time-resolved measurement (delay=50 µs; gate time=400 µs). The ratio of the fluorescence at 665 nm to the fluorescence at 620 nm is then calculated as described above.

The reaction of the anti-TBP monoclonal antibody with the TBP suppresses the FRET signal measured beforehand between the anti-IP1-TBP and the IP1-d2. Only the FRET signal that exists between the anti-cAMP-TBP5COOH and the cAMP-d2 is detected during this second reading of the microplate.

Figure 14:
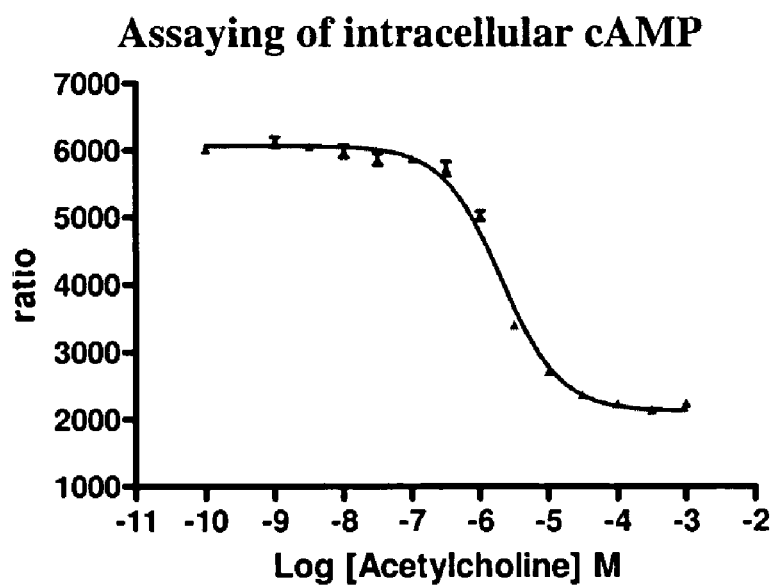
FIG. 14: Change in FRET signal representative of the amount of cAMP produced by the cell as a function of the concentration of acetylcholine present in the medium. The decrease in the FRET signal results from the production of cAMP by the cell, via a competition phenomenon (see example 8).

As shown in FIG. 14, as the production of intracellular cAMP increases following the stimulation of the M1 receptor with acetylcholine, the HTRF ratio decreases. This is because the cAMP produced by the cells competes with the cAMP-d2 for binding the anti-cAMP-TBP5COOH and thus decreases the FRET signal.

LITERATURE REFERENCES

Lynch B A, Minor C, Loiacono K A, van Schravendijk M R, Ram M K, Sundaramoorthi R, Adams S E, Phillips T, Holt D, Rickles R J, MacNeil I A Simultaneous assay of Src SH3 and SH2 domain binding using different wavelength fluorescence polarization probes. *Anal Biochem.* 1999 275(1): 62-73

Blommel P, Hanson G T, Vogel K W Multiplexing fluorescence polarization assays to increase information content per screen: applications for screening steroid hormone receptors. *J Biomol Screen.* 2004 9(4):294-302

Swartzman et Al. An homogeneous and multiplexed immunoassay for high-throughput screening using fluorometric microvolume assay technology. *Anal. Biochem.* (1999), 271, 143-151

Chan-Hui P Y, Stephens K, Warnock R A, Singh S Applications of eTag trade mark assay platform to systems biology approaches in molecular oncology and toxicology studies. *Clin Immunol.* 2004 111(2):162-74

Tian H, Cao L, Tan Y, Williams S, Chen L, Matray T, Chema A, Moore S, Hernandez V, Xiao V, Tang M, Singh S Multiplex mRNA assay using electrophoretic tags for high-throughput gene expression analysis. *Nucleic Acids Res.* 2004 32(16):e126

Bradford J A, Buller G, Suter M, Ignatius M, Beechem J M Fluorescence-intensity multiplexing: simultaneous seven-marker, two-color immunophenotyping using flow cytometry. *Cytometry A.* 2004 61(2):142-52

Kurner J M, Klimant I, Krause C, Pringsheim E, Wolfbeis O S A new type of phosphorescent nanospheres for use in advanced time-resolved multiplexed bioassays. *Anal Biochem.* 2001 297(1):32-41

Tong A K, Li Z, Jones G S, Russo J J, Ju J Combinatorial fluorescence energy transfer tags for multiplex biological assays. *Nat. Biotechnol.* 2001 19(8):756-9

Tyagi S, Marras S A, Kramer F R Wavelength-shifting molecular beacons. *Nat. Biotechnol.* 2000 18(11):1191-6

Watt et Al. *Immunochemistry* 1997, 14,533-541

Babendure J R, Adams S R, Tsien R Y Aptamers switch on fluorescence of triphenylmethane dyes. *J Am Chem Soc.* 2003 125(48):14716-7

The invention claimed is:

1. A method for detecting 2 biological events in a reaction medium, comprising employing 2 pairs of fluorescent FRET partner conjugates, each pair comprising a donor fluorophore and an acceptor fluorophore, $\lambda 1$ being the excitation wavelength of the donor fluorophores and $\lambda 2$ being the emission wavelength of the acceptor fluorophores, said method comprising:
   (i) bringing the reaction medium into contact with a first pair of fluorescent FRET partner conjugates specific for a first biological event;
   (ii) exciting the reaction medium at the wavelength $\lambda 1$;
   (iii) measuring the FRET signal emitted by the reaction medium at the wavelength $\lambda 2$ and corresponding to the first biological event;
   (iv) introducing into the reaction medium a FRET signal killer specific for the first pair of fluorescent FRET partner conjugates brought into contact in step (i);
   (v) bringing the reaction medium into contact with a pair of fluorescent FRET partner conjugates specific for a second biological event different from the first biological event detected in the preceding steps;
   (vi) exciting the reaction medium at the wavelength $\lambda 1$;
   (vii) measuring the FRET signal emitted by the reaction medium at the wavelength $\lambda 2$, corresponding to the second biological event for which the pair of fluorescent FRET partner conjugates brought into contact in step (v) is specific.

2. The method according to claim 1, comprising applying at least one stimulation step to the reaction medium, wherein the at least one stimulation step is of chemical, pharmacological, electrical, thermal or mechanical nature.

3. The method according to claim 2, wherein the at least one stimulation step comprises adding an agonist, an antagonist, an inverse agonist or an allosteric modulator of a receptor.

4. The method according to claim 1, wherein each of the fluorescent FRET partner conjugates comprises a fluorophore covalently bound to a probe, this probe being specific for the first biological event or the second biological event, and wherein said probe consists of a molecule involved in the first biological event or the second biological event, or else comprises a domain for binding to a molecule involved in the first biological event or the second biological event.

5. The method according to claim 4, wherein the probe is a molecule involved in the first biological event or the second biological event and wherein molecule is a protein, a peptide, an enzyme, an enzyme substrate, an intracellular messenger, a cyclic nucleotide, a phospholipid, a transcription factor, a compound comprising an inositol ring, a nucleic acid or an oligonucleotide.

6. The method according to claim 5, wherein the probe comprises a domain for binding to a molecule involved in the first biological event or the second biological event, and wherein the domain is:
   an antibody or antibody fragment;
   an anti-tag antibody or antibody fragment which recognizes a tag grafted on the molecule involved in the first biological event or the second biological event of any performance of step (v);
   an aptamer;
   a peptide;
   a protein; or
   a single-stranded nucleic acid which optionally hybridizes with a nucleic acid of complementary sequence covalently bound to the molecule involved in said biological event.

7. The method according to claim 4, wherein a donor fluorophore or an acceptor fluorophore of a pair of fluorescent FRET partner conjugates is a luminescent protein, a fluorescent protein extracted from coral; a phycobiliprotein; a luminescent organic molecule; a rare earth cryptate; a rare earth chelate or a luminescent inorganic particle.

8. The method according to claim 1, wherein the FRET signal killer is a compound which binds specifically to one of the donor fluorophore and acceptor fluorophore of any of the pairs of fluorescent FRET partner conjugates to bring about a decrease of at least 70% of said signal.

9. The method according to claim 8, wherein the FRET signal killer is a compound which is an antibody or a fragment thereof, a peptide or an aptamer, and wherein the compound has a binding domain for one of the donor fluorophore and acceptor fluorophore of any of the pairs of fluorescent FRET partner conjugates.

10. The method according to claim 8, wherein one of the pairs of fluorescent FRET partner conjugates comprises a rare earth cryptate or chelate and wherein, the FRET signal killer is an antibody or an antibody fragment; a peptide; or an aptamer, and wherein the FRET signal killer has a binding domain for a rare earth chelate or cryptate.

11. The method according to claim 1, wherein at least one of the donor fluorophore and acceptor fluorophore of a pair of fluorescent FRET partner conjugates consists of a fluorophore which is covalently coupled to a first single-stranded nucleic acid, the complementary strand of which is covalently attached to a molecule involved in a biological event for which a pair of fluorescent partner conjugates is specific, or is covalently coupled to a molecule which recognizes a molecule involved in said biological event, and wherein the FRET signal killer is a single-stranded nucleic acid, the sequence of which is complementary to said first single-stranded nucleic acid.

12. The method according to claim 1, wherein at least one of the pairs of fluorescent FRET partner conjugates comprises a rare earth chelate, and in that the FRET killer for said FRET signal is an ion which competes with the rare earth for the complexing with the rare earth chelate or a chelating agent which competes with the rare earth chelate for the complexing with the rare earth.

13. The method according to claim 1, wherein at least one of the pairs of fluorescent FRET partner conjugates comprises a rare earth chelate or cryptate, and in that the FRET killer for said FRET signal is an agent which induces oxidation-reduction reactions at the level of the rare earth.

14. The method according to claim 1, wherein at least one of the pairs of fluorescent FRET partner conjugates is sensitive to pH in that the FRET killer for said FRET signal is a pH modifier.

15. The method according to claim 1, wherein the first biological event or the second biological event is
an enzyme reaction;
a presence or a variation in concentration of a protein, an enzyme, an enzyme substrate, an intracellular messenger, a phospholipid, a transcription factor, a compound comprising an inositol ring, a nucleic acid or a growth factor;
two molecules coming closer together in the reaction medium; or
a modification to the three-dimensional conformations of the molecule.

16. A method for suppressing a FRET signal emitted by a pair of FRET fluorophore partners, wherein one of the FRET fluorophore partners is a rare earth cryptate, comprising using an antibody which specifically recognizes said rare earth cryptate.

* * * * *